(12) United States Patent
Ko et al.

(10) Patent No.: US 10,142,768 B2
(45) Date of Patent: Nov. 27, 2018

(54) SYSTEM FOR AND METHOD OF PROVIDING SERVICE RELATED TO OBJECT

(71) Applicant: SAMSUNG ELECTRONICS CO., LTD., Gyeonggi-do (KR)

(72) Inventors: Jae-woo Ko, Uiwang-si (KR); Tae-hwan Wi, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 334 days.

(21) Appl. No.: 14/015,020

(22) Filed: Aug. 30, 2013

(65) Prior Publication Data

US 2014/0066096 A1 Mar. 6, 2014

(30) Foreign Application Priority Data

Aug. 31, 2012 (KR) .......................... 10-2012-0096652

(51) Int. Cl.
| | |
|---|---|
| *H04W 24/00* | (2009.01) |
| *H04W 4/02* | (2018.01) |
| *G06Q 10/08* | (2012.01) |
| *G06Q 30/00* | (2012.01) |
| *G06Q 30/02* | (2012.01) |

(Continued)

(52) U.S. Cl.
CPC .............. *H04W 4/02* (2013.01); *G06Q 10/08* (2013.01); *G06Q 10/0833* (2013.01); *G06Q 30/01* (2013.01); *G06Q 30/0251* (2013.01); *G06Q 30/0282* (2013.01); *G06Q 30/0623* (2013.01); *G06Q 30/0631* (2013.01); *G06Q 30/0639* (2013.01); *G06Q 50/12* (2013.01); *G06Q 50/22* (2013.01)

(58) Field of Classification Search
CPC ... H04W 4/008; H04W 76/023; H04W 84/12; H04W 4/023
See application file for complete search history.

(56) References Cited

U.S. PATENT DOCUMENTS 7,598,866 B2 * 10/2009 Hayashi ................. G06Q 30/06
340/572.1
8,229,461 B1 * 7/2012 Manroa .................. H04W 4/025
455/414.2

(Continued)

FOREIGN PATENT DOCUMENTS

| CN | 102224744 A | 10/2011 |
|---|---|---|
| CN | 102224764 A | 10/2011 |

(Continued)

OTHER PUBLICATIONS

Communication dated Oct. 22, 2013 issued by the European Patent Office in counterpart European Patent Application No. 13182439.3.

(Continued)

*Primary Examiner* — Khalid Shaheed
(74) *Attorney, Agent, or Firm* — Sughrue Mion, PLLC

(57) ABSTRACT

A system for and a method of providing service related to an object include receiving property information of the object when the device is located within a predetermined distance from the object, requesting available service from a server based on a current location of the device receiving the property information and the received property information, and receiving the requested service from the server.

26 Claims, 21 Drawing Sheets

(51) Int. Cl.
 G06Q 30/06 (2012.01)
 G06Q 50/12 (2012.01)
 G06Q 50/22 (2018.01)

(56) References Cited

U.S. PATENT DOCUMENTS

| | | |
|---|---|---|
| 8,559,884 B2 | 10/2013 | Dolfini et al. |
| 2004/0171379 A1 | 9/2004 | Cabrera et al. |
| 2006/0107037 A1* | 5/2006 | Lincoln .................. G06F 21/12 |
| | | 713/155 |
| 2006/0202803 A1* | 9/2006 | Yoon .................... G06K 7/0008 |
| | | 340/10.4 |
| 2007/0006098 A1 | 1/2007 | Krumm et al. |
| 2007/0016479 A1 | 1/2007 | Lauper |
| 2007/0263069 A1 | 11/2007 | Jendbro |
| 2008/0162141 A1 | 7/2008 | Lortz |
| 2009/0018899 A1* | 1/2009 | Ogushi ............ G06Q 10/06311 |
| | | 705/7.13 |
| 2009/0076912 A1* | 3/2009 | Rajan .................... G06Q 30/02 |
| | | 705/14.64 |
| 2009/0171559 A1* | 7/2009 | Lehtiniemi ............ G01C 21/20 |
| | | 701/533 |
| 2009/0325484 A1* | 12/2009 | Lele ...................... H04W 8/205 |
| | | 455/41.1 |
| 2010/0056047 A1* | 3/2010 | Bertin ............... H04M 1/72525 |
| | | 455/41.1 |
| 2010/0069115 A1 | 3/2010 | Liu |
| 2010/0169153 A1 | 7/2010 | Hwacinski et al. |
| 2011/0087685 A1 | 4/2011 | Lin et al. |
| 2011/0199192 A1* | 8/2011 | Buckner ............ G06K 19/0724 |
| | | 340/10.51 |
| 2012/0021684 A1 | 1/2012 | Schultz et al. |
| 2012/0042036 A1 | 2/2012 | Lau et al. |
| 2013/0005243 A1* | 1/2013 | Royston ............... H04B 5/0043 |
| | | 455/41.1 |
| 2013/0059534 A1* | 3/2013 | Sobalvarro ............ G06Q 30/02 |
| | | 455/41.1 |
| 2013/0218983 A1* | 8/2013 | Richard ................ H04W 12/02 |
| | | 709/206 |
| 2015/0067154 A1* | 3/2015 | Ly ...................... H04L 43/0876 |
| | | 709/224 |

FOREIGN PATENT DOCUMENTS

| | | |
|---|---|---|
| CN | 102549548 A | 7/2012 |
| EP | 1 995 922 A2 | 11/2008 |
| EP | 2 124 146 A1 | 11/2009 |
| GB | 2 454 042 A | 4/2009 |
| JP | 2006-99299 A | 4/2006 |
| KR | 10-2010-0136659 A | 12/2010 |
| KR | 10-2012-0005468 A | 1/2012 |
| RU | 63 627 U1 | 5/2007 |
| WO | 2009/079407 A2 | 6/2009 |
| WO | 2010087747 A1 | 8/2010 |

OTHER PUBLICATIONS

Communications dated Dec. 2, 2013 issued by the International Searching Authority in counterpart International Application No. PCT/KR2013/007808 (PCT/ISA/210 & PCT/ISA/237).
Communication dated Apr. 27, 2016, issued by Russian Intellectual Property Office in counterpart Russian Application No. 2015111148/08(017427).
Communication dated Aug. 18, 2017 by the State Intellectual Property Office of P.R. China in counterpart Chinese Application No. 201380045552.8.
Communication dated Jan. 24, 2017 by the State Intellectual Property Office of P.R. China in counterpart Chinese Patent Application No. 201380045552.8.
Communication dated Apr. 25, 2018, issued by the State Intellectual Property Office of P.R. China in counterpart Chinese Application No. 201380045552.8.
Communication dated Jul. 2, 2018, issued by the Korean Intellectual Property Office in counterpart Korean Application No. 10-2012-0096652.

* cited by examiner

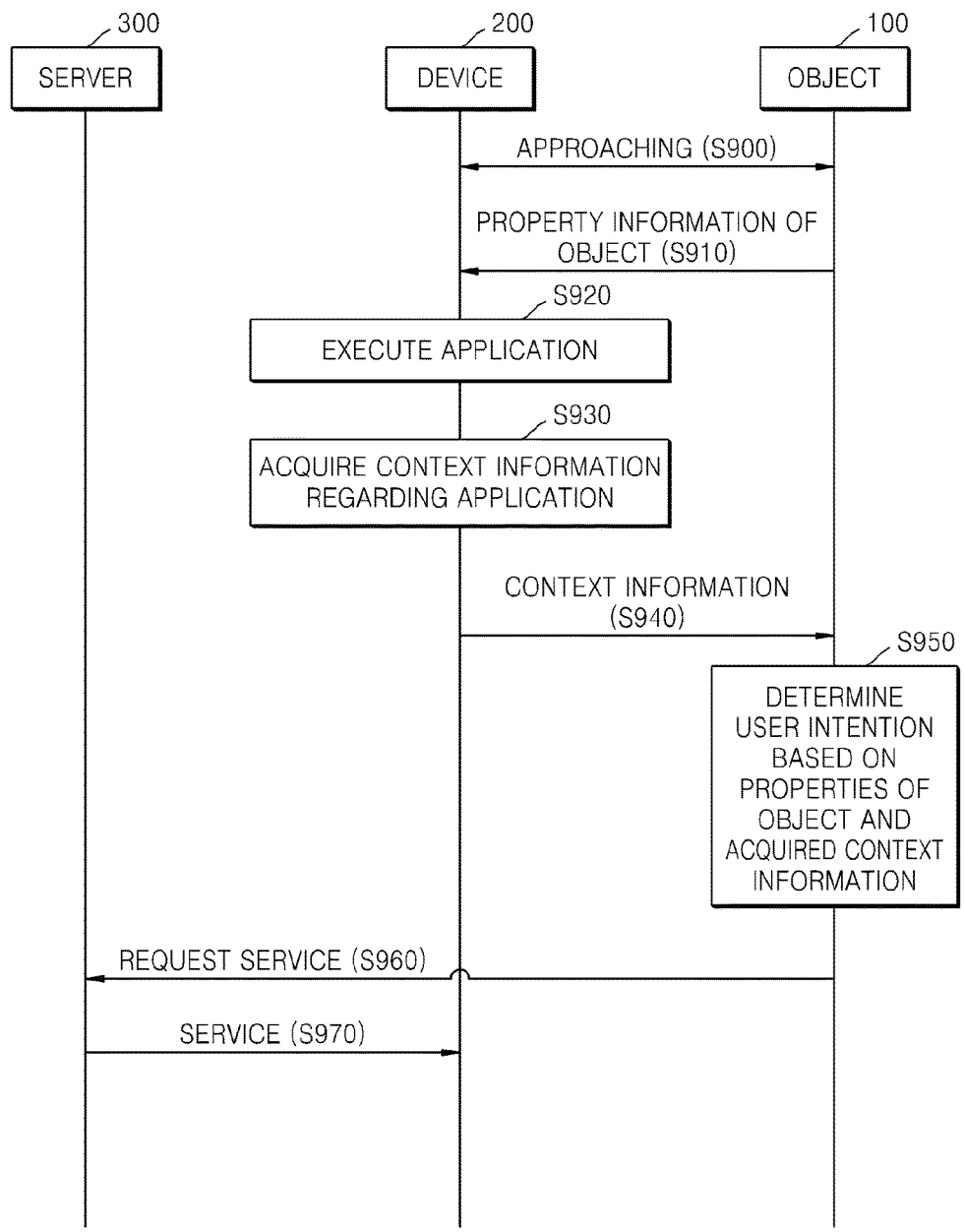

FIG. 10

| TYPE OF SERVICE (10) | CONTEXT INFORMATION (12) ||||||||
|---|---|---|---|---|---|---|---|---|
| | DEVICE-RELATED INFORMATION (14) ||| USER-RELATED INFORMATION (16) |||||
| | CURRENT LOCATION | CURRENT TIME | CURRENT WEATHER | PREVIOUSLY EXECUTED APPLICATION | JOB | CONSTITUTION | HEALTH CONDITION | FAMILY/ ACQUAINTANCE | PREFERENCE | ... |
| FOOD SUPPLY | O | O | O | SEARCH CRITERIA: ALLERGY | O | O | O | | | ... |
| CONCERT | O | O | | PAYMENT: ORCHESTRA | O | | | O | O | ... |
| MOVIE | O | O | | O | O | | | O | O | ... |
| COSMETICS | O | | | O | O | O | | O | O | ... |
| EVENT INFORMATION | | | | O | | | | | O | ... |
| ... | ... | ... | ... | ... | ... | ... | ... | ... | ... | ... |

(a)  (b)

SYSTEM FOR AND METHOD OF PROVIDING SERVICE RELATED TO OBJECT

CROSS-REFERENCE TO RELATED PATENT APPLICATION

This application claims the benefit of Korean Patent Application No. 10-2012-0096652, filed on Aug. 31, 2012, in the Korean Intellectual Property Office, the disclosure of which is incorporated herein in its entirety by reference.

BACKGROUND

1. Field

Methods and apparatuses consistent with exemplary embodiments relate to providing service that is related to objects nearby a device.

2. Description of the Related Art

Due to recent developments in information communication technologies and network technologies, multimedia-type portable devices may include various functions. Recently, near-distance communication units are have been integrated in such devices, and thus information services for utilizing information received from tags included in objects are available.

Previously, advertisement information corresponding to tag information attached to an advertisement poster was provided to a device for display to a user. However, since information unilaterally defined by an advertiser is provided to a device, a user of the device cannot receive proper services that satisfy his or her needs.

Therefore, techniques for determining an intention of a user using a near-distance communication and effectively providing services satisfying the intention of the user are necessary.

SUMMARY

Aspects of exemplary embodiments provide a system for and a method of providing a predetermined service that is related to objects to a device based on properties of the object and context information related to the properties of the object.

Aspects of exemplary embodiments also provide a system for and a method of providing a predetermined service that is related to objects to a device based on context information regarding an intention of a user in relation to services.

According to an aspect of an exemplary embodiment, there is provided a method by which a device receives a service related to an object, the method including receiving property information of the object when the device is located within a predetermined distance from the object; requesting a server for an available service related to the object based on a current location of the device and the received property information; and receiving the requested service from the server.

The requesting of the available service includes determining types of the available service and types of specific information to be provided by the available service based on the received property information and the current location of the device; and requesting the server for the available service based on the types of the available service and the types of the specific information.

The method further includes acquiring context information related to the types of the available service and the types of the specific information, wherein the requesting the server for the available service based on the types of the available service and the types of the specific information comprises providing the acquired context information to the server.

The receiving of the requested service includes receiving the service based on the types of the available service, the types of the specific information, and the context information.

The acquiring of the context information includes acquiring context information related to an application being executed by the device.

The context information includes information related to at least one of a date, a time, the current location of the device, a gender of a user, an age of the user, and an execution history of an application that is executed by the device in relation to the available service.

The acquired context information is provided to the server via the object.

The requesting of the available service includes requesting the server for the available service based on time, a user profile of the user, and a user history of services used by the user.

The property information of the object includes information related to services related to the object and at least one of an identifier of the object and information related to applications related to the services.

The receiving of the property information includes receiving the property information via a close-distance communication network.

The property information is property information related to an object selected based on a user input via the device.

The property information is provided by the object to the device based on a user input for selecting from a predetermined list displayed on a screen of the object.

The receiving of the requested service includes receiving specific information to be provided by a type of service selected based on the received property information and the current location of the device from the server.

In the requesting of the available service, the available service are requested from the server via the object, in the receiving of the requested service, specific information to be provided by a type of service selected based on the received property information of the object and the current location of the device is received from the server, and the specific information to be provided by the type of service selected based on the received property information and the current location of the device is determined by the object.

According to another aspect of an exemplary embodiment, there is provided a method by which a device receives a service related to an object, the method including determining an application executed by the device when the device is located within a predetermined distance from the object; requesting a server to provide an available service based on types of services provided by the application and a current location of the device; and receiving the requested service from the server.

According to another aspect of an exemplary embodiment, there is provided a method by which a server provides a service related to an object, the method including receiving from the device property information of the object and a current location of a device; determining specific information to be provided by a service related to the object to be provided to the device based on the received property information and the current location of the device; and providing the specific information to the device, wherein the property information of the object is provided by the object to the device when the device is located within a predetermined distance from the object.

According to another aspect of an exemplary embodiment, there is provided a method by which an object provides a service related to the object to a device, the method including providing property information of the object to the device; receiving context information related to properties of the object acquired by the device based on the property information; and providing a service related to the object determined based on the received context information to the device, wherein the service is related to the object, and wherein the context information is provided by the device to the object when the device is located within a predetermined distance from the object.

According to another aspect of the present invention, there is provided a device which receives a service related to an object, the device including a property information receiving unit configured to receive property information of the object when the device is located within a predetermined distance from the object; a service requesting unit configured to request a server for an available service related to the object based on a current location of the device and the received property information; and a service receiving unit configured to receive the requested service from the server.

According to another aspect of the an exemplary embodiment, there is provided a server which provides a service related to an object, the server including a context information acquiring unit configured to acquire property information of the object and a current location of a device from the device; and a service providing unit configured to provide specific information to be provided by a service related to the object, to the device, wherein the service is determined based on the received property information and the current location of the device, and wherein the property information of the object is provided by the object to the device when the device is located within a predetermined distance from the object.

According to another aspect of an exemplary embodiment, there is provided an object which provides a service related to the object, the object including a property information providing unit configured to provide property information of the object to the device; a context information acquiring unit configured to acquire context information related to properties of the object acquired by the device based on the provided property information from the device; and a service providing unit configured to provide the device a service related to the object determined based on the received context information, wherein the context information is provided by the device to the object when the device is located within a predetermined distance from the object.

BRIEF DESCRIPTION OF THE DRAWINGS

The above and other aspects will become more apparent by describing in detail exemplary embodiments thereof with reference to the attached drawings in which:

FIG. 9 is a flowchart showing a method by which the object acquires intention information related to services and provides services to the device via the server, according to an exemplary embodiment;

FIG. 10 is a diagram showing an example of a context information table indicating context information in correspondence to types of services, according to an exemplary embodiment;

DETAILED DESCRIPTION OF EXEMPLARY EMBODIMENTS

Figure 1:
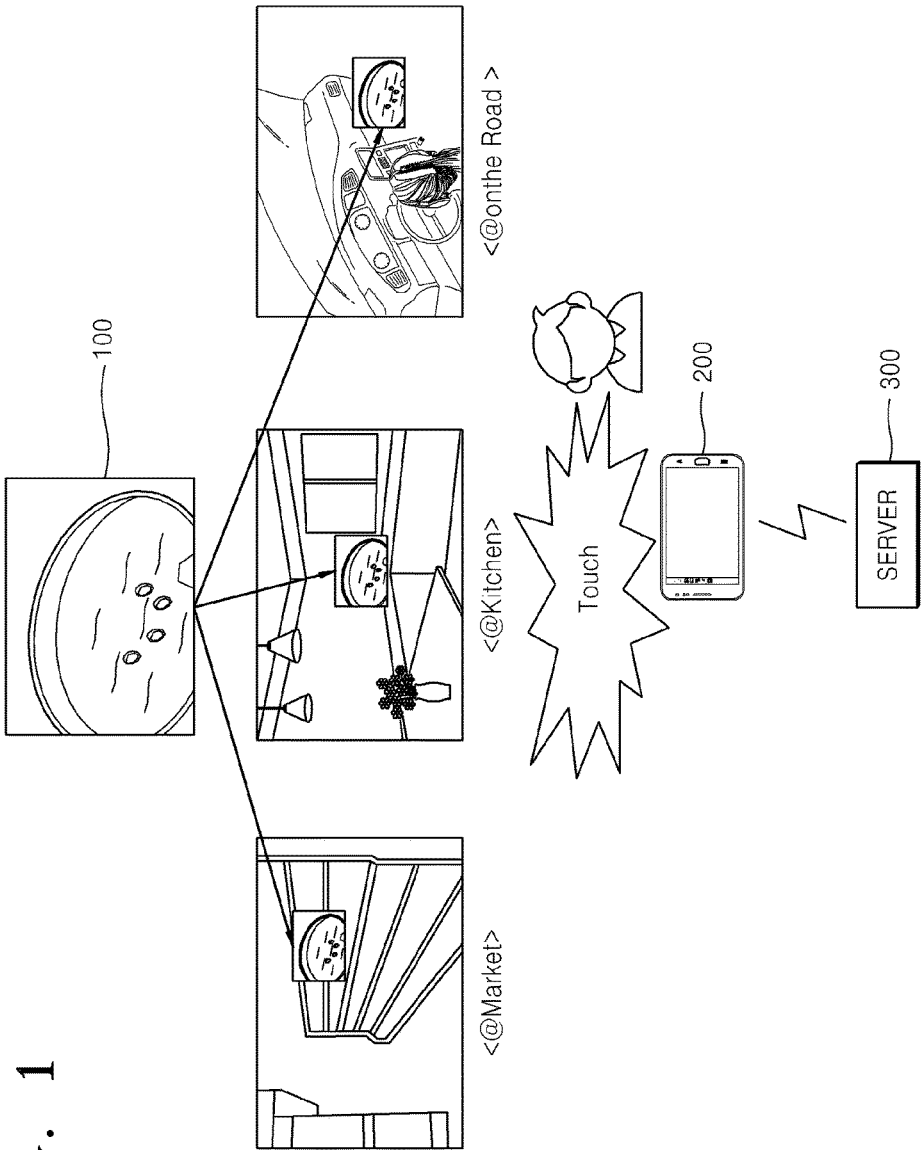
FIG. 1 is a diagram showing a service-providing system that provides services related to objects according to an exemplary embodiment.

Exemplary embodiments will now be described more fully with reference to the accompanying drawings. The exemplary embodiments may, however, be embodied in many different forms and should not be construed as being limited to the exemplary embodiments set forth herein; rather, these exemplary embodiments are provided so that this disclosure will be thorough and complete, and will fully convey the concept of the disclosure to those skilled in the art. Like reference numerals in the drawings denote like elements.

When a component is referred to as being "connected to" another component, it can not only be "directly connected," but also "electrically connected" across an intervening device. Furthermore, when a unit is referred to as "comprising" or "including" a component(s), it does not exclude other components unless stated otherwise and shall be referred to as comprising or including the other components.

Hereinafter, an object is goods or a device including a marker or a tag attached to the object for performing close-distance communication. The object may include a QR code, a barcode, a RFID tag, or a NFC tag. Furthermore, the object may include a passive smart poster (PSP) or an active smart poster (ASP). However, the object is not limited thereto. If the object includes a NFC tag, the NFC tag may include a NFC data exchange format (NDEF) data.

Furthermore, a service refers to a service for providing information corresponding to an intention of a user and may include a recipe service, a navigation service, a goods information providing service, a map information providing service, a ticketing service, a coupon providing service, and a goods purchase service, for example.

Furthermore, property information of an object is information regarding properties of the object and may include information related to an identifier of the object, a type of the object, applications related to the object, and services related to the object.

Furthermore, context information may include context information related to a device and context information related to a user. The context information related to a device may include a location of the device, time, weather, and an execution history of applications executed by the device. Furthermore, the context information related to a user may include information related to gender, age, job, name, relationship, nationality, handicap, constitution, health conditions, and preferences of the user.

Furthermore, intention information is information related to services a user wants to receive and may include information regarding types of services and types of specific information to be provided by the services. For example, intention information may include "a recipe for spicy taste."

Furthermore, context information related to intention information refers to context information for providing a service corresponding to an intention of a user. Context information related to intention information may be extracted from context information acquired by a device.

Furthermore, a device that approaches an object refers to a device is located within a predetermined communication range of an object.

Hereinafter, exemplary embodiments will be described in detail with reference to the attached drawings.

FIG. 1 is a diagram showing a service-providing system that provides services related to objects according to an exemplary embodiment.

As shown in FIG. 1, the service-providing system according to an exemplary embodiment includes an object 100, a device 200, and a server 300. A user's intention may vary based on context of a user and types of object 100 which device 200 of the user approaches, and the service-providing system according to an exemplary embodiment may provide services satisfying intentions of the user to the device 200 based on properties of the object 100 and a context of the device 200.

The object 100 may provide the device 200 with information regarding properties of the object 100 and link information for the device 200 to receive services. The object 100 may be a device that includes a marker or a tag for near-distance communication.

The object 100 may include a QR code, a barcode, a RFID tag, or a NFC tag, and the object 100 may be an advertisement poster or a smart poster for providing predetermined information. Furthermore, in the service-providing system according to an exemplary embodiment, a smart poster technique defined by the NFC Forum may be employed, but is not limited thereto.

Furthermore, the object 100 may be disposed at various locations. For example, the object 100 may be included in a street advertisement panel, a magazine, a poster, goods, or a public transportation station. Furthermore, if the object 100 is a smart poster related to 'soup,' for example, the object 100 may be located in a market, in a kitchen, or along a street.

Furthermore, the device 200 collects property information regarding properties of the object 100 if the device 200 and the object 100 are located within communication range of each other. The device 200 may receive services satisfying intentions of a user of the device 200 based on context information related to the properties of the object 100. The context information may include context information related to the device 200 and context information related to a user. The context information related to the device 200 may include information regarding a location of the device 200, time, weather, and a history of application execution by the device 200, for example. The history of application execution may include information regarding titles, reproduction dates, reproduction times, and authors of contents reproduced via applications on the device 200. Furthermore, the context information related to a user may include information regarding at least one from among gender, age, job, name, relationship, nationality, handicap, constitution, health condition, and preferences of the user. Context information related to gender, age, nationality, and handicap of a user may be acquired based on resident registration number and passport number of the user. Furthermore, information related to job, constitution, health condition, relationship, and preferences of a user may be acquired based on messages input via the device 200 by the user (e.g., SMS messages, MMS messages, and SNS messages). Furthermore, information related to preferences of a user may include information regarding types of services used by the user and the user's evaluations on the services. Furthermore, if a user makes payments via the device 200, information related to preferences of the user may be generated based on a history of the payments. The context information related to the device 200 and the context information related to the user may be updated as the device 200 receives services via the object 100 and the server 300.

For example, if the object 100 is a smart poster related to 'soup' and the device 200 is within communication range of the object 100 located in a market, the device 200 may receive a service indicating whether family members of a user of the device 200 are allergic to the 'soup' and a service identifying the location of the 'soup' in the market from the server 300.

Furthermore, if the object 100 is a smart poster related to 'soup' and the device 200 is close to the object 100 located in a kitchen, the device 200 may receive a service for providing a spicy soup recipe for cooking the 'soup' from the server 300.

For example, if the object 100 is a smart poster related to 'soup' and the device 200 is within communication range of the object 100 located along a street, the device 200 may receive a service for navigating to a store selling the 'soup'.

Furthermore, the device 200 may be a smart phone, a mobile phone, a personal digital assistant (PDA), a laptop, a media player, a global positioning system (GPS) device, or any of various other mobile or non-mobile computing devices. However, the device 200 is not limited thereto.

The server 300 may receive from the device at least one from among property information related to the object 100, context information related to the object 100, and intention information related to the device 200, and may provide services corresponding to the intention of the device 200.

With a service-providing system according to an exemplary embodiment, a user may check for allergic reactions based on information regarding the user's constitution and medical information before the user purchases food supplies, and may determine nutrients that help health of the user.

Furthermore, a user may determine a particular bus to take to a predetermined destination and a period of time to wait at a bus stop until the particular bus arrives, for example.

Furthermore, if the object 100 is a concert poster, for example, a user may purchase a desired ticket when the device 200 is within communication range of the object 100.

Furthermore, if the object 100 is a magazine, for example, a user may download discount coupons for goods advertised in the magazine when the device 200 is within communication range of the object 100.

Furthermore, if the object 100 is an event poster located at a predetermined event location, a user may receive a navigation service to navigate to an event location when the device 200 is within communication range of the object 100.

Furthermore, a user may purchase goods by when the device 200 is within communication range of the object 100, for example.

Figure 2:
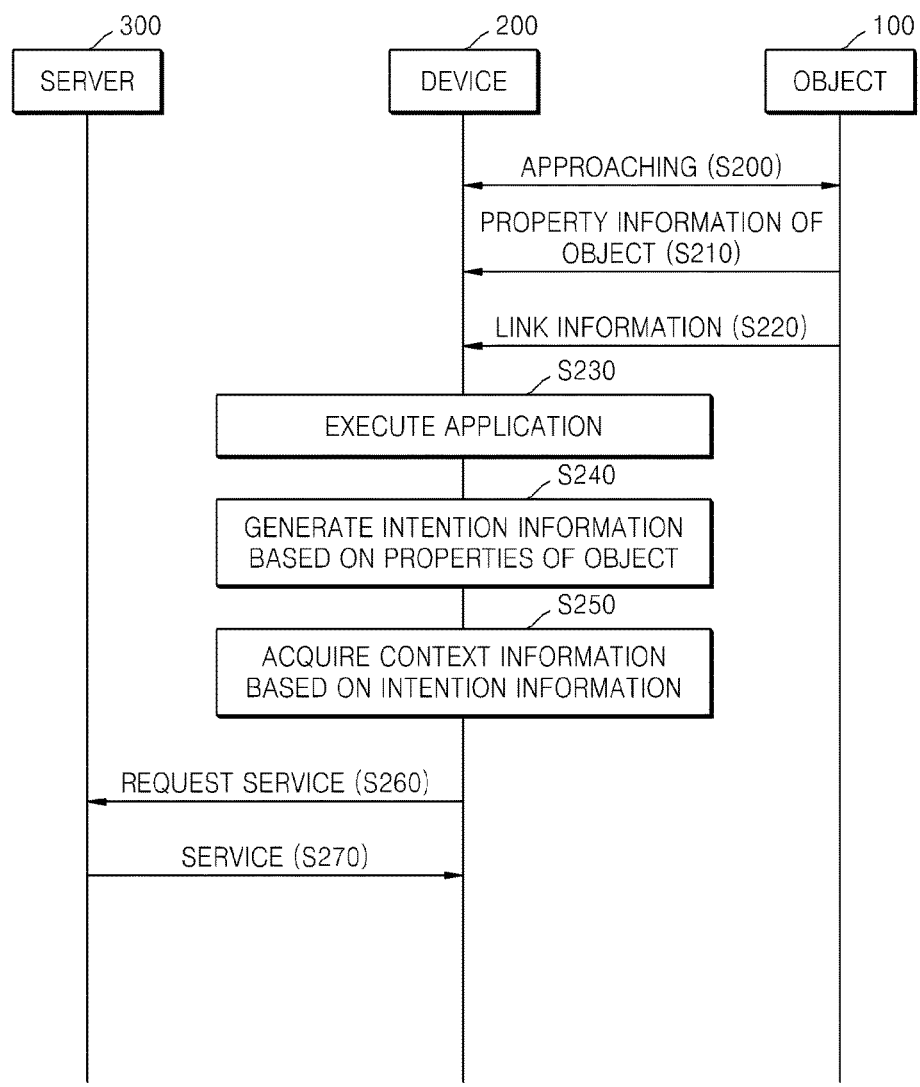
FIG. 2 is a flowchart showing a method by which a device generates intention information based on properties of an object and receives services from a server.

FIG. 2 is a flowchart showing a method by which the device generates intention information based on properties of the object and receives services from the server.

In an operation S200, the device 200 approaches the object 100. The device 200 and the object 100 may be connected to each other via a communication network. For example, the device 200 and the object 100 may be connected to each other via a near field communication (NFC) network.

In an operation S210, the device 200 receives property information related to properties of the object 100 from the object 100. The property information of the object 100 is information related to properties of the object 100 and may include information regarding an identifier of the object 100, a type of the object 100, applications related to the object 100, and services related to the object 100. As the device 200 accesses the object 100 via an NFC channel, the device 200 may receive property information related to properties of the object 100 from the object 100. The property information of the object 100 will be described below in closer detail with reference to FIG. 12.

In an operation S220, the device 200 receives link information for receiving services related to the object 100 from the object 100. The link information may include a link address of the server 300 which provides services related to the object 100.

In an operation S230, the device 200 executes an application for receiving services. The device 200 may execute an application for receiving services based on application information included in the property information of the object 100. If an application for receiving services is not installed on the device 200, the device 200 may download a predetermined application and install the downloaded application. Furthermore, if an application for receiving services is installed on the device 200, the device 200 may execute the installed application. A method by which the device 200 downloads an application will be described below in closer detail with reference to FIG. 18.

Furthermore, although it is described above that, in the operation S230, an application is executed after the device 200 approaches the object 100 and receives property information of the object 100, the method is not limited thereto. An application for receiving services may be executed by the device 200 in advance, and the device 200 may approach to the object 100 and receive property information of the object 100 from the object 100 while the application is being executed.

In an operation S240, the device 200 generates intention information based on properties of the object 100. The intention information is information related to services a user wants to receive and may include information regarding types of services and types of specific information to be provided by the services.

In an operation S240, the device 200 may determine types of services based on the properties of the object 100 and may determine types of specific information to be provided by the services. For example, if the object 100 is an advertisement poster related to 'soup,' the device 200 may select from among information related to an allergic reaction checking service, a recipe providing service, and a navigation service.

If the device 200 decides to provide a recipe providing service, the device 200 may determine specific information to be provided by the recipe providing service. For example, the specific information to be provided by the recipe providing service may include a recipe using an oven, a recipe using a microwave, and a recipe using a gas stove, and the device 200 may decide to provide the recipe using a microwave.

Furthermore, if the device 200 decides to provide a navigation service, the device 200 may determine specific information to be provided by the navigation service. For example, the specific information to be provided by the navigation service may include navigation information regarding roads designated for 4-wheeled vehicles, navigation information regarding toll-free roads, 3-dimensional navigation information, 2-dimensional navigation information, and navigation information provided via a heads up display (HUD) device, in which the device 200 may provide the navigation information regarding toll-free roads and the 2-dimensional navigation information.

Furthermore, the device 200 may determine types of services based on location of the device 200 and properties of the object 100 and may determine types of specific information to be provided by the determined services.

Types of services and types of specific information to be provided by services may be determined based on properties of the object 100 and user inputs. However, the services and information are not limited thereto, and types of services and types of specific information to be provided by services may be determined based on context information as described below. Furthermore, in the operation S240, the device 200 may determine types of services only and may not determine specific information to be provided by services.

In an operation S250, the device 200 acquires context information based on intention information. For example, if type of a service included in the intention information is 'recipe providing service' and type of specific information to be provided by the corresponding service is a 'recipe using an oven,' the device 200 may acquire information regarding preferred tastes of a user as context information.

Furthermore, if type of a service included in the intention information is 'navigation service' and types of specific information to be provided by the corresponding service are 'navigation information regarding toll-free roads' and '2-dimensionally provided navigation information,' the device 200 may acquire information regarding location of the device 200 and type of a vehicle as context information.

Although it is described above that, in the operation S250, context information is acquired based on intention information, the context information is not limited thereto. The device 200 may acquire context information related to the device 200 and context information related to a user in advance and may extract context information related to intention information from the pre-acquired context information. In this case, the pre-acquired context information may be used by the device 200 to generate intention information in the operation S240.

Furthermore, context information may be acquired by an application that is either being executed or has been executed by the device 200. For example, if an application being executed by the device 200 is an application for receiving recipes, context information related to recipes may be acquired.

In an operation S260, the device 200 requests a service from the server 300. The device 200 may provide property information of the object 100 and intention information and context information acquired by the device 200 to the server 300. For example, the device 200 may provide information indicating that the object 100 is a smart poster related to 'soup,' a 'recipe providing service' and a 'recipe using an oven' are necessary, and a user prefers spicy taste to the server 300. In this case, the device 200 may access the server 300 by using the link information received in the operation S220 and request for the corresponding service from the server 300.

Furthermore, the device 200 may request a service from the server 300 based on time, the user's profile, and the user's history of using services.

In an operation S270, the server 300 may provide a service to the device 200 based on the received information. For example, the server 300 may provide information regarding a recipe for using an 'oven' to cook a 'soup' having a 'spicy taste' to the device 200.

Figure 3:
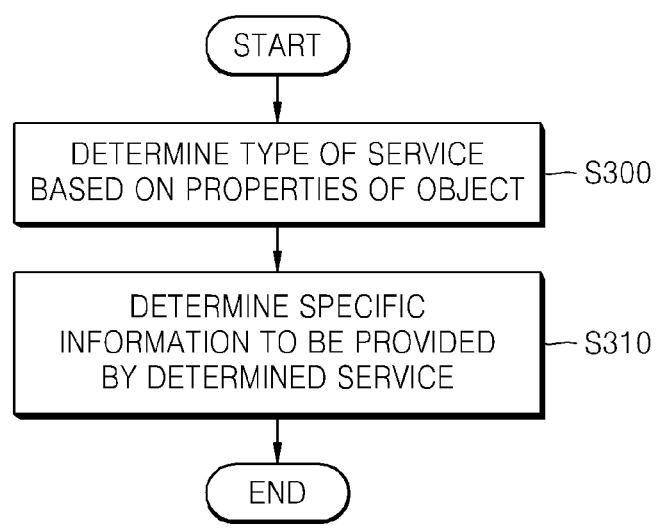
FIG. 3 is a flowchart showing a method by which the device generates intention information related to services, according to an exemplary embodiment.

FIG. 3 is a flowchart showing a method by which the device 200 generates intention information related to services, according to an exemplary embodiment.

In an operation S300, the device 200 determines types of services based on properties of the object 100. In the operation S300, the device 200 may decide at least one service from among services that may be provided by the server 300 based on properties of the object 100. For example, if the object 100 is an advertisement poster for 'soup,' the device 200 may select from among an allergic reaction checking service, a recipe providing service, and a navigation service. The device 200 may receive a list of services related to the object 100 from the object 100 when the device 200 approaches the object 100. However, the services are not limited thereto. Information regarding types of services corresponding to properties of the object 100 may be stored in the device 200 in advance. Furthermore, the device 200 may also determine types of services based on location of the device 200 and properties of the object 100.

In an operation S310, the device 200 may determine types of specific information to be provided by a decided on service. Furthermore, if the device 200 decides to provide a recipe providing service in the operation S300, the device 200 may determine specific information to be provided by the recipe providing service. For example, the specific information to be provided by the recipe providing service may include a recipe using an oven, a recipe using a microwave, and a recipe using a gas stove, and the device 200 may select the recipe using a microwave.

Furthermore, if the device 200 decides to provide navigation service in the operation S300, the device 200 may determine specific information to be provided by the navigation service. For example, the specific information to be provided by the navigation service may include navigation information regarding roads designated for 4-wheeled vehicles, navigation information regarding toll-free roads, 3-dimensional navigation information, 2-dimensional navigation information, and navigation information provided via a heads up display (HUD) device, in which the device 200 may provide the navigation information regarding toll-free roads and the 2-dimensional navigation information.

Types of services and types of specific information to be provided by services may be determined based on properties of the object 100 and user inputs. However, the services and specific information are not limited thereto, and types of services and types of specific information to be provided by services may be determined based on context information acquired by and stored in the device 200 in advance. Types of specific information to be provided by services may be determined based on age, gender, job, health condition, and preference of a user. In this case, types of services and types of specific information to be provided by services may be recommended by the device 200, and the type of predetermined service and the type of predetermined specific information to be provided by the corresponding service may be determined based on a user input.

Furthermore, services provided by the server 300 may be categorized according to ages, genders, jobs, and health conditions of users, for example. In this case, there may be particular link information for receiving services of corresponding categories from the server 300 per service category, and the server 300 may provide a predetermined link to the device 200.

Figure 4:
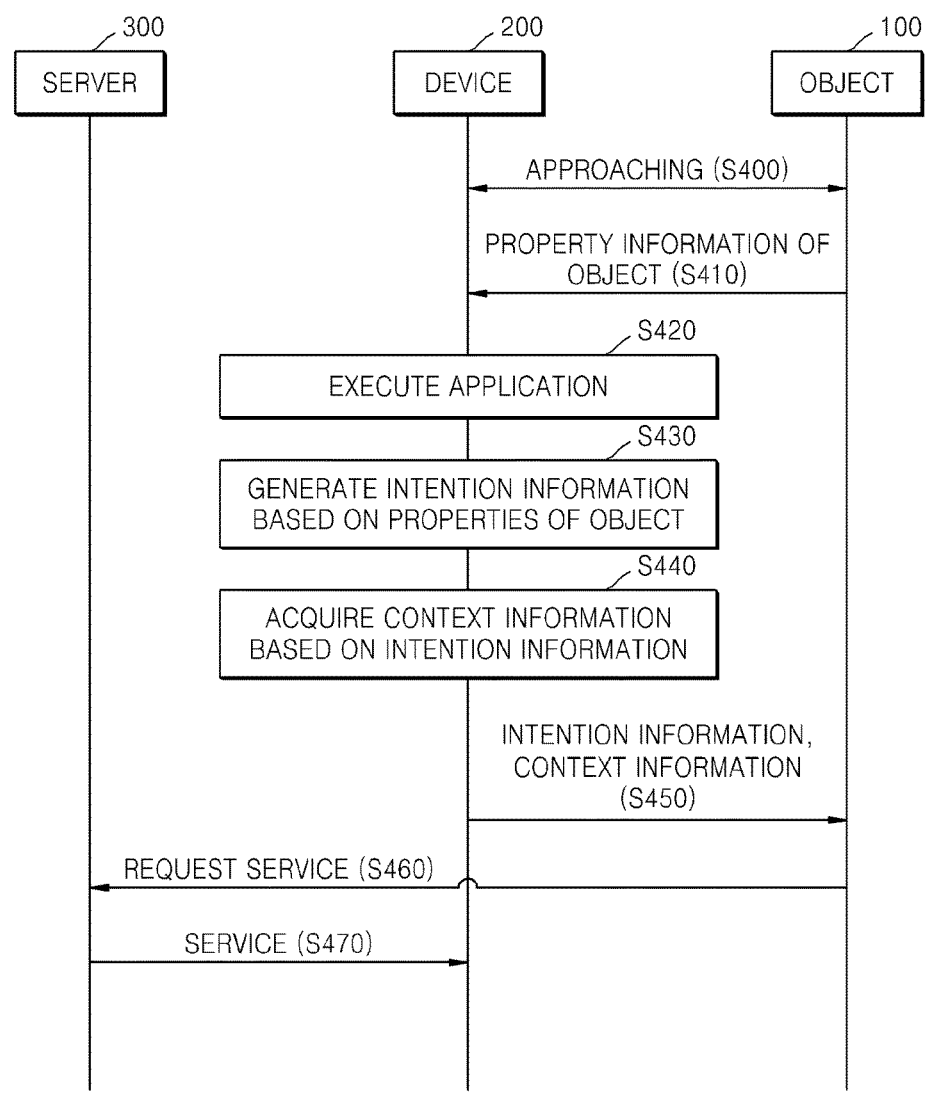
FIG. 4 is a flowchart for showing a method by which the device generates intention information based on properties of the object and requests a service from a server, according to an exemplary embodiment.

FIG. 4 is a flowchart for showing a method by which the device generates intention information based on properties of the object and requests a service from the server, according to an exemplary embodiment. In FIG. 4, the device 200 may provide acquired intention information and context information to the object 100. Furthermore, the object 100 may request the server 300 to provide a predetermined service to the device 200.

Operations S400 through S440 are similar to the operations S200, S210, S230, and S250 of FIG. 3, and thus only operations S450 through S470 will be described below.

In an operation S450, the device 200 provides intention information and context information to the object 100. For example, the device 200 may provide intention information indicating that 'recipe providing service' and a 'recipe using an oven' are necessary and intention information indicating that a user prefers a spicy taste to the object 100.

In an operation S460, the object 100 requests the server 300 to provide a predetermined service to the device 200. The object 100 may provide information indicating that the object 100 is a smart poster related to 'soup,' a 'recipe providing service' and a 'recipe using an oven' are necessary, and a user prefers spicy taste to the server 300.

In an operation S470, the server 300 provides a corresponding service to the device 200 based on received information. For example, the server 300 may provide information regarding a recipe for using an 'oven' to cook 'soup' having a 'spicy taste' to the device 200.

The object 100 may request a service from the server 300 and provide specific information related to the service to the device 200 simultaneously.

Furthermore, although it is described that the server 300 provides a service directly to the device 200 in FIG. 4, the service provision is not limited thereto. In response to a request from the object 100, the server 300 may provide a predetermined service to the device 200 via the object 100.

Figure 5:
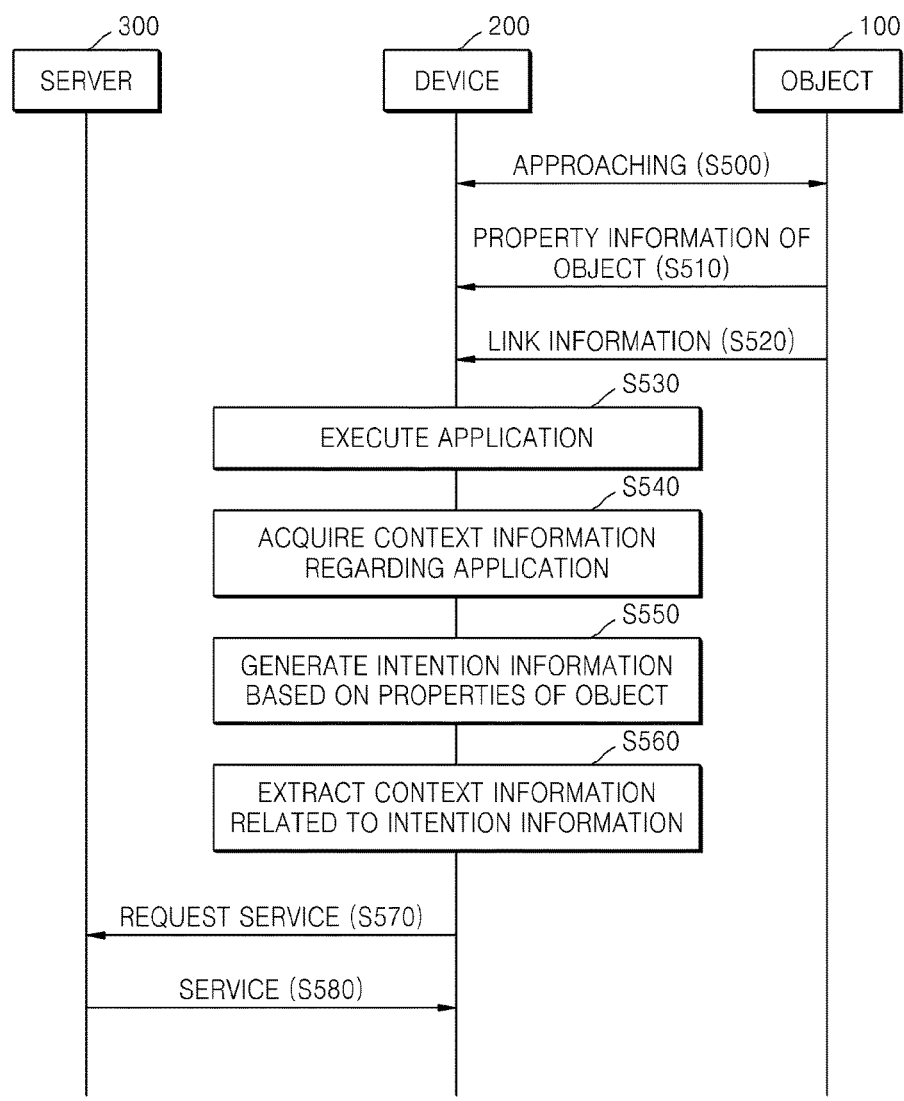
FIG. 5 is a flowchart showing a method by which the device acquires context information related to an application that is being executed by the device and receives a service from the server, according to an exemplary embodiment.

FIG. 5 is a flowchart showing a method by which the device 200 acquires context information related to an application that is being executed by the device 200 and receives a service from the server 300, according to an exemplary embodiment. When the device 200 is located within a pre-set distance from the object 100, the device 200 may check at least one application executed by the device 200 and may request the server 300 for available services based on types of services that are provided by the application and information regarding location of the device 200.

In an operation S500, the device 200 approaches the object 100. The device 200 may be within a predetermined distance from the object 100, and the device 200 and the object 100 may be connected to each other via a communication network. For example, the device 200 and the object 100 may be connected to each other via an NFC network.

In an operation S510, the device 200 receives property information related to properties of the object 100 from the object 100. The property information of the object 100 is information related to properties of the object 100 and may include information regarding from among an identifier of the object 100, a type of the object 100, applications related to the object 100, and services related to the object 100. The property information of the object 100 will be described below in closer detail with reference to FIG. 12.

In an operation S520, the device 200 receives link information for receiving services related to the object 100 from the object 100. The link information may include a link address of the server 300 which provides services related to the object 100.

In an operation S530, the device 200 executes an application for receiving services from the server 300. The device 200 may execute an application for receiving services based on application information included in the property information of the object 100. If an application for receiving services is not installed on the device 200, the device 200 may download a predetermined application and install the downloaded application. Furthermore, if an application for receiving services is installed on the device 200, the device 200 may execute the installed application. A method by which the device 200 downloads an application will be described below in closer detail with reference to FIG. 18.

Furthermore, although it is described above that, in the operation S530, an application is executed after the device 200 approaches the object 100 and receives property information of the object 100, the application execution is not limited thereto. An application for receiving services may be executed by the device 200 in advance, and the device 200 may approach the object 100 and receive property information of the object 100 from the object 100 while the application is being executed.

In an operation S540, the device 200 may acquire context information related to applications that are being executed. In the operation S540, the device 200 may determine applications that are being executed, determine types of services provided by the applications that are being executed, and acquire context information related to the determined services. Furthermore, the device 200 may check an execution history of the applications that are being executed and may acquire context information from the execution history. For example, if an application provides an 'allergic reaction checking service,' a 'recipe providing service,' and a 'navigation service,' the device 200 may acquire context information necessary for checking an allergic reaction, providing recipes, and providing navigation information. For example, in relation to the 'allergic reaction checking service,' the device 200 may acquire information regarding constitution and health conditions of a user as context information. As another example, in relation to the 'recipe providing service,' the device 200 may acquire information regarding age, gender, and preferred tastes of a user as context information. As a last example, in relation to the 'navigation service,' the device 200 may acquire information regarding location of the device 200, weather, and traffic conditions as context information.

However, acquiring the context information is not limited thereto, and the device 200 may acquire various types of context information.

In an operation S550, the device 200 generates intention information based on properties of the object 100. The intention information is information related to services a user wants to receive and may include information regarding types of services and types of specific information to be provided by the services.

In the operation S550, the device 200 may determine types of services based on the properties of the object 100 and may determine types of specific information to be provided by the services. The device 200 may select services related to properties of the object 100 from among services provided by an application being executed.

For example, if the object 100 is an advertisement poster related to a 'soup,' the device 200 may select a recipe providing service or a navigation service from among services provided by an application.

If the device 200 decides to provide a recipe providing service, the device 200 may determine specific information to be provided by the recipe providing service. For example, the specific information to be provided by the recipe providing service may include a recipe using an oven, a recipe using a microwave, and a recipe using a gas stove, and the device 200 may decide to provide the recipe using a microwave.

Furthermore, if the device 200 decides to provide a navigation service, the device 200 may determine specific information to be provided by the navigation service. For example, the specific information to be provided by the navigation service may include navigation information regarding roads designated for 4-wheeled vehicles, navigation information regarding toll-free roads, 3-dimensional navigation information, 2-dimensional navigation information, and navigation information provided via a heads up display (HUD) device, in which the device 200 may provide the navigation information regarding toll-free roads and the 2-dimensional navigation information.

Types of services and types of specific information to be provided by services may be determined based on properties of the object 100 and user inputs. However, the determination of services and information is not limited thereto, and types of services and types of specific information to be provided by services may be automatically determined based on properties of the object 100 and properties of an application. Furthermore, in the operation S540, the device

200 may determine types of services only and may not determine specific information to be provided by services.

Furthermore, the device 200 may determine types of services based on location of the device 200 and applications being executed and may determine types of specific information to be provided by the determined services. The device 200 may select a service related to the location of the device 200 from among services that are provided by an application being executed. Information regarding locations at which predetermined services are to be provided may be pre-set and stored in the device 200 or the server 300 in advance.

In an operation S560, the device 200 extracts context information related to intention information from the context information acquired in the operation S540. The device 200 may extract only information related to types of services and specific information to be provided by the services included in the intention information from among various information included in the context information acquired in the operation S540. Although it is described above that context information related to the intention information generated in the operation S550 is extracted, the context information acquisition is not limited thereto. The device 200 may not acquire any context information before the operation S560 and may only acquire context information related to intention information after the intention information is generated. In this case, the device 200 may acquire context information related to types of services and specific information to be provided by the services included in the intention information.

In an operation S570, the device 200 requests the server 300 for a service. The device 200 may provide property information of the object 100 and intention information and context information acquired by the device 200 to the server 300. The device 200 may receive a request of acquired context information from the object 100 and may provide the context information to the object 100 in response to the request. For example, the device 200 may provide information indicating that the object 100 is a smart poster related to a 'soup,' a 'recipe providing service' and a 'recipe using an oven' necessary for preparing the soup, and preference indicating a user prefers spicy taste to the server 300. In this case, the device 200 may access the server 300 by using the link information received in the operation S520 and request the server 300 for the corresponding service.

In an operation S580, the server 300 may provide a service to the device 200 by using the received information. For example, the server 300 may provide information regarding a recipe for using an oven to cook a 'soup' having a 'spicy taste' to the device 200.

Figure 6:
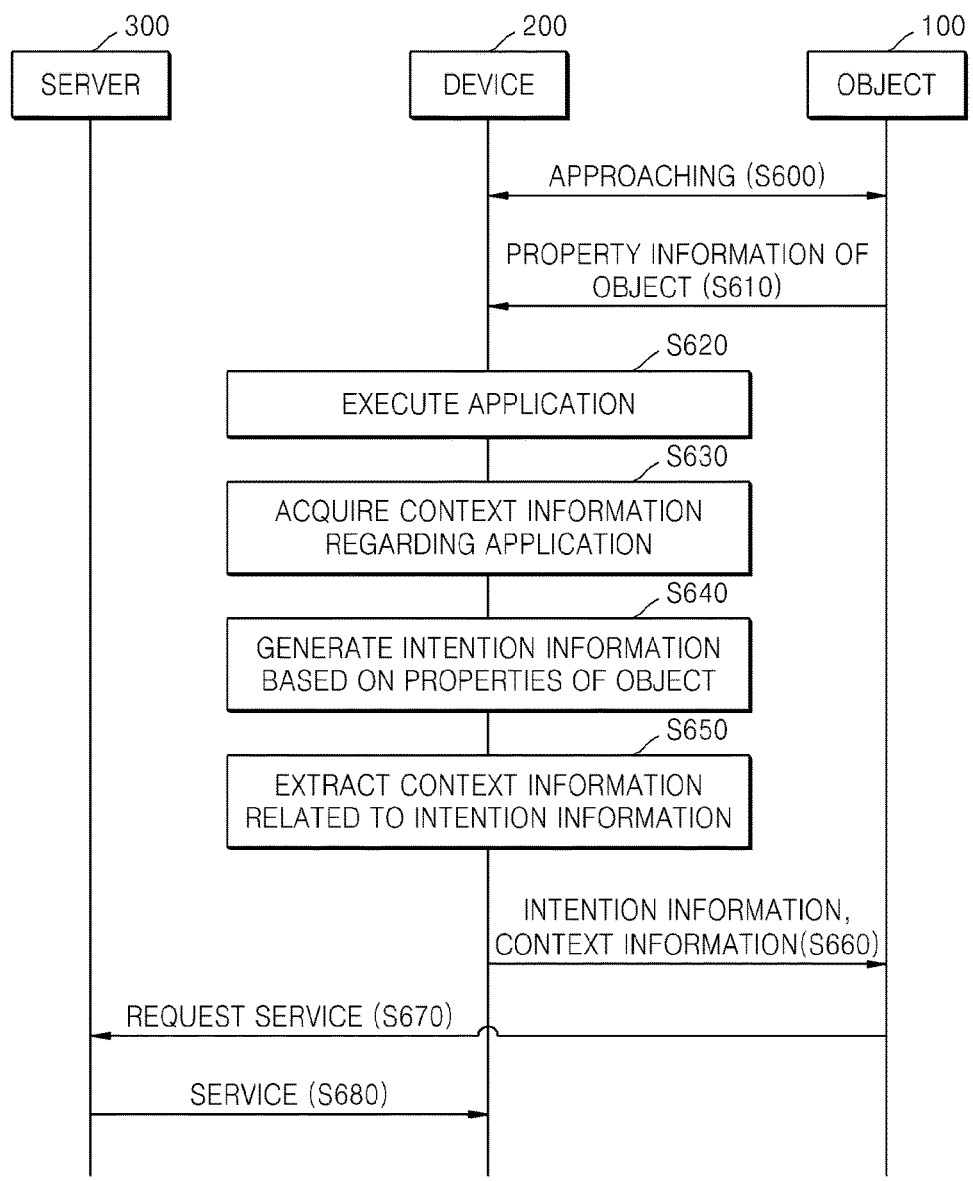
FIG. 6 is a flowchart for showing a method by which the device acquires context information related to an application that is being executed by the device and requests the server for a service, according to an exemplary embodiment.

FIG. 6 is a flowchart for showing a method by which the device 200 acquires context information related to an application that is being executed by the device 200 and requests the server 300 for a service, according to an exemplary embodiment. In FIG. 6, the device 200 may provide acquired intention information and context information to the object 100. Furthermore, the object 100 may request the server 300 to provide a predetermined service to the device 200.

Operations S600 through S650 of FIG. 6 correspond to the operations S500, S510, and S530 through S560 of FIG. 5, and thus only operations S660 through S680 will be described below.

In an operation S660, the device 200 provides intention information and context information to the object 100. For example, the device 200 may provide intention information indicating that a 'recipe providing service' and a 'recipe using an oven' are necessary and context information indicating that a user prefers 'spicy taste' to the object 100.

In an operation S670, the object 100 requests the server 300 to provide a predetermined service to the device 200. The object 100 may provide information indicating that the object 100 is a smart poster related to a 'soup,' a 'recipe providing service' and a 'recipe using an oven' are necessary, and a user prefers 'spicy taste' to the server 300.

In an operation S680, the server 300 provides a corresponding service to the device 200 based on received information. For example, the server 300 may provide information regarding a recipe for using an 'oven' to cook a 'soup' having a 'spicy taste' to the device 200.

The object 100 may request a service to the server 300 and provide specific information related to the service to the device 200 simultaneously.

Furthermore, although it is described that the server 300 provides a service directly to the device 200 in FIG. 6, the service provision is not limited thereto. In response to a request from the object 100, the server 300 may provide a predetermined service to the device 200 via the object 100.

Figure 7:
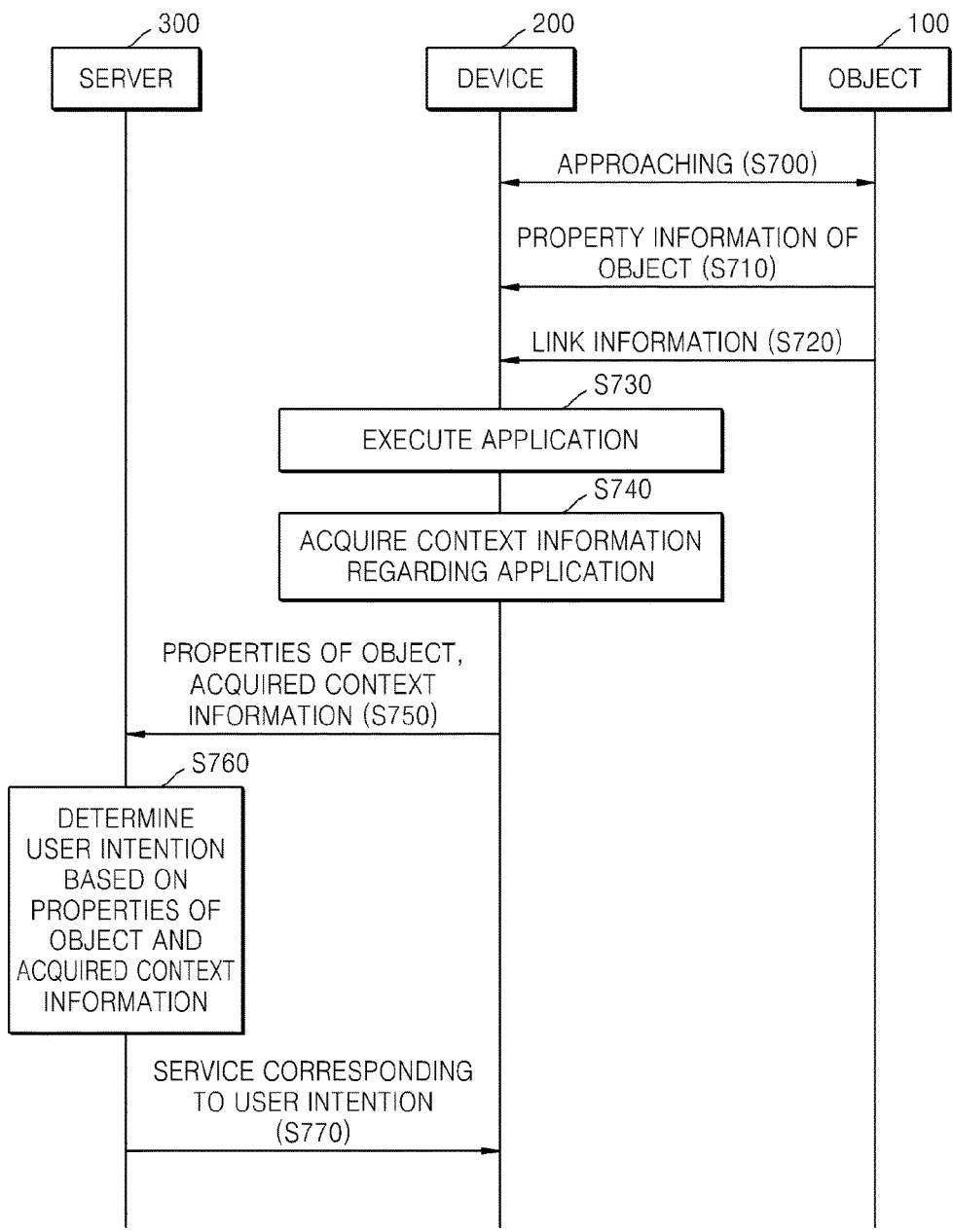
FIG. 7 is a flowchart showing a method by which the device acquires intention information related to services and provides services to the device.

FIG. 7 is a flowchart showing a method by which the device 200 acquires intention information related to services and provides services to the device 200. In FIG. 7, the server 300 may determine an intention of a user based on properties of the object 100 and context information acquired by the device 200, and may provide services corresponding to the determined intention to the device 200. Furthermore, the server 300 may determine an intention of a user based on properties of the object 100 and location of the device 200.

Operations S700 through S730 of FIG. 7 correspond to the operations S200 through S230 of FIG. 2, and thus only operations S740 through S770 will be described below.

In an operation S740, the device 200 may acquire context information based on properties of the object 100. In the operation S740, the device 200 may check properties of the object 100 and acquire context information related to the services related to the object 100. For example, if services related to the object 100 are an 'allergic reaction checking service,' a 'recipe providing service,' and a 'navigation service,' the device 200 may acquire context information necessary for checking an allergic reaction, providing recipes, and providing navigation information. For example, in relation to the 'allergic reaction checking service,' the device 200 may acquire information regarding constitution and health conditions of a user as context information. As another example, in relation to the 'recipe providing service,' the device 200 may acquire information regarding age, gender, and preferred tastes of a user as context information. As a last example, in relation to the 'navigation service,' the device 200 may acquire information regarding location of the device 200, weather, and traffic conditions as context information.

However, the context information acquisition is not limited thereto, and the device 200 may acquire various types of context information. For example, the device 200 may acquire information related to an execution history of the applications executed by the device 200, gender of a user, job of the user, etc.

In an operation S750, the device 200 provides property information of the object 100 related to properties of the object 100 and the acquired context information to the server 300. The device 200 may provide information related to an identifier of the object 100, a list of services related to the object 100, and identifiers of applications related to the object 100 to the server 300. Furthermore, the device 200 may provide context information acquired in relation to 'allergic reaction checking service,' recipe providing service,' and 'navigation service' to the server 300. Furthermore, the device 200 may provide information related to an execution history of the applications executed by the device 200, gender of a user, job of the user, etc. to the server 300.

In an operation S760, the server 300 may determine an intention of a user based on properties of the object 100 and acquired context information. The device 200 may determine types of services and may determine types of specific information to be provided by the services. Furthermore, if the server 300 determines a plurality of services and a plurality of specific information to be provided by the services, the server 300 may recommend types of the determined services and types of the specific information to be provided by the services to the device and may receive information related to types of services and types of specific information to be provided by the services from the device 200.

Furthermore, the device 200 may determine types of services and types of specific information to be provided by the services based on location of the device 200 and properties of the object 100.

In an operation S770, the server 300 may provide a service and specific information to be provided by the service to the device 200 by using the received information. For example, the server 300 may provide information regarding a recipe for using an oven to cook a 'soup' having a 'spicy taste' to the device 200.

Figure 8:
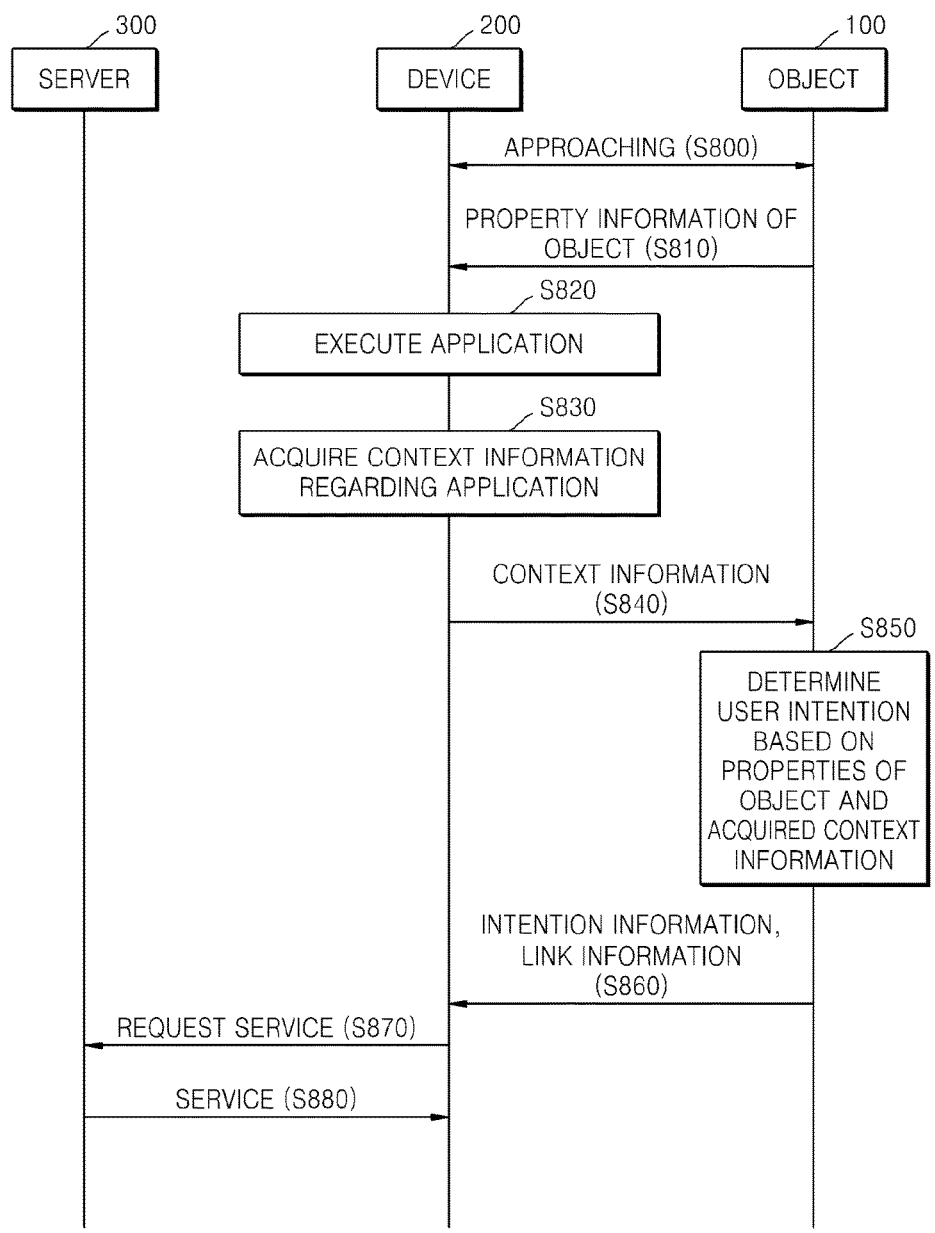
FIG. 8 is a flowchart for showing a method by which the object acquires intention information related to services and provides the intention information to the device according to an exemplary embodiment.

FIG. 8 is a flowchart for showing a method by which the object 100 acquires intention information related to services and provides the intention information to the device 200, so that the server 300 provides a service to the device 200, according to an exemplary embodiment. In FIG. 8, the object 100 may determine an intention of a user based on context information acquired from the device 200 and may provide services corresponding to the determined intention to the device 200. Furthermore, the object 100 may determine an intention of a user based on properties of the object 100 and location of the device 200.

Furthermore, services provided by the server 300 may be categorized according to ages, genders, jobs, and health conditions of users, for example. In this case, there may be particular link information for receiving services of corresponding categories from the server 300 per service category, and the server 300 may provide a predetermined link to the device 200.

Operations S800 through S830 of FIG. 8 correspond to the operations S700 through S730 of FIG. 7, and thus only operations S840 through S870 will be described below.

In an operation S840, the device 200 provides acquired context information to the object 100. The device 200 may provide context information acquired in relation to the 'allergic reaction checking service,' 'recipe providing service,' and 'navigation service' to the server 300. Furthermore, the device 200 may provide information related to an execution history of the applications executed by the device 200, gender of a user, job of the user, etc. to the server 300.

In an operation S850, the object 100 may determine an intention of a user based on properties of the object 100 and acquired context information. The object 100 may determine types of services and may determine types of specific information to be provided by the services. Furthermore, if the object 100 determines a plurality of services and a plurality of specific information to be provided by the services, the object 100 may recommend types of the determined services and types of the specific information to be provided by the services to the device and may receive information related to types of services and types of specific information to be provided by the services from the device 200.

In an operation S860, the object 100 provides intention information regarding an intention of a user and link information for receiving services to the device 200. The link information may include a link address of the server 300 which provides services related to the object 100.

In an operation S870, the device 200 requests the server 300 for a service. The device 200 may provide property information of the object 100 and intention information and context information acquired by the device 200 to the server 300. The device 200 may extract context information related to received intention information. However, the context information extraction is not limited thereto. Context information related to intention information may be extracted by the object 100, and the device 200 may receive the context information related to the intention information from the object 100. For example, the device 200 may provide information indicating that the object 100 is a smart poster related to a 'soup,' a 'recipe providing service' and a 'recipe using an oven' are necessary, and a user prefers 'spicy taste' to the server 300. In this case, the device 200 may access the server 300 by using the link information and request for the corresponding service from the server 300.

In an operation S880, the server 300 provides a corresponding service to the device 200 based on received information. For example, the server 300 may provide information regarding a recipe for using an oven to cook a 'soup' having a 'spicy taste' to the device 200.

FIG. 9 is a flowchart showing a method by which the object 100 acquires intention information related to services and provides services to the device 200 via the server 300, according to an exemplary embodiment. In FIG. 8, the object 100 may request the server 300 to provide services to the device 200.

Operations S900 through S950 of FIG. 9 correspond to the operations S800 through S850 of FIG. 8, and thus only operations S960 and S970 will be described below.

In an operation S960, the object 100 requests the server 300 for a service. The object 100 may request the server 300 to provide the service to the device 200. The object 100 may provide property information of the object 100, received intention information, and context information related to the intention information to the server 300. The context information related to the intention information may be extracted by the object 100 based on the intention information. For example, the object 100 may provide information indicating that the object 100 is a smart poster related to a 'soup,' a 'recipe providing service' and a 'recipe using an oven' are necessary, and a user prefers 'spicy taste' to the server 300.

In an operation S970, the server 300 may provide a corresponding service to the device 200 based on received information. For example, the server 300 may provide information regarding a recipe for using an oven to cook a 'soup' having a 'spicy taste' to the device 200.

Although it is described above that the object 100 requests the server 300 for a service in FIG. 9, the exemplary embodiment is not limited thereto. The object 100 may not request the server 300 for a service. In this case, the object 100 may provide specific information to be provided by the service stored in the object 100 to the device 200.

Furthermore, although it is described above that the server 300 provides a service directly to the device 200 in FIG. 9, the service provision is not limited thereto. In response to a request from the object 100, the server 300 may provide a predetermined service to the device 200 via the object 100.

FIG. 10 is a diagram showing an example of a context information table indicating context information in correspondence to types of services, according to an exemplary embodiment.

Referring to FIG. 10, a context information table according to an exemplary embodiment may include a service type field 10, a context information field 12, a device related information field 14, and a user-related information field 16.

The service type field 10 may include service identifiers, e.g., 'food supply,' 'concert,' 'movie,' 'cosmetics,' and 'event information.' Furthermore, the context information field 12 may include context information related to predetermined services. Referring to FIG. 10, context information related to a current location of the device 200, current time, an application executed by the device 200, a job of a user, family/acquaintances of the user, and user preferences are related to a concert-related service.

Furthermore, although FIG. 10 does not show specific information included in the context information field 12, the context information field 12 may include specific information. The device related information field 14 may include context information related to the device 200. The device related information field 14 may include information related to a current location of the device 200, current time, current weather, and the type of application executed by the device 200. Furthermore, the user related information field 16 may include context information related to a user. The user related information field 16 may include information related to a job, constitution, health condition, family/acquaintances, and preferences of the user.

Figure 11:
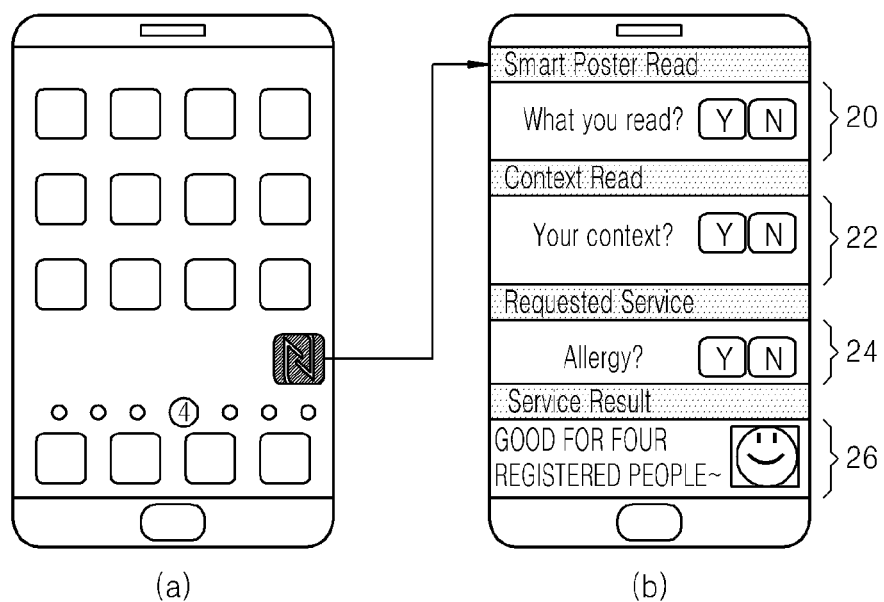
FIG. 11 is a diagram showing an example menu screen image of an application executed by the device, according to an exemplary embodiment.

FIG. 11 is a diagram showing an example menu screen image of an application executed by the device 200, according to an exemplary embodiment.

Referring to FIG. 1, when a predetermined icon is selected in a screen image on the device 200 as shown in FIG. 11(a), an initial screen image of an application for receiving services related to an object 100 may be displayed as shown in FIG. 11(b). The initial screen image of the application may include a region 20 for displaying properties of the object 100, a region 22 for displaying context information, a region 24 for displaying intention information (e.g., requested service), and a region 26 for displaying specific information to be provided by a service.

Figure 12:
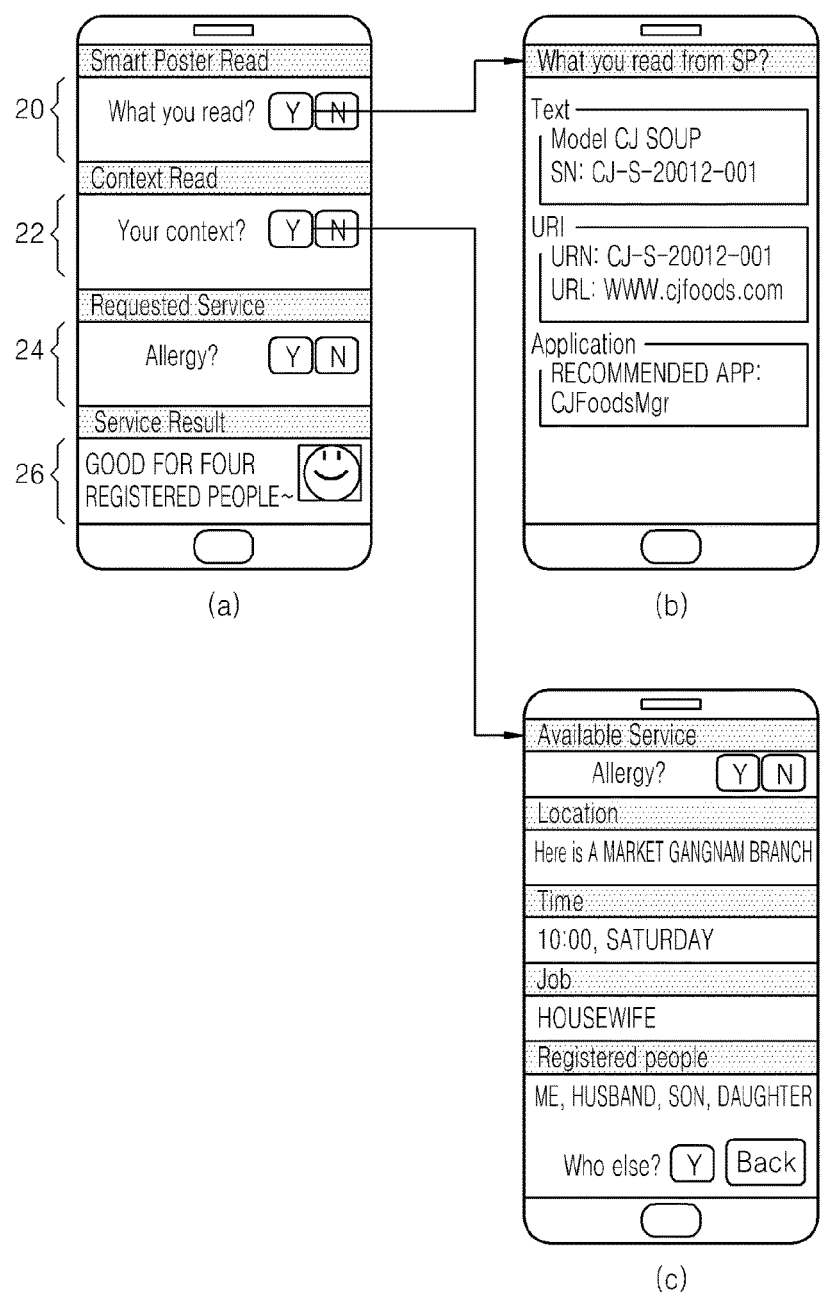
FIG. 12 is a diagram showing an example in which a service-providing system and context information related to the device are displayed via an application.

FIG. 12 is a diagram showing an example in which a service-providing system and context information related to the device 200 are displayed via an application.

When a predetermined icon in the region 20 for displaying properties of the object 100 in the initial screen image of an application as shown in FIG. 12(a) is selected, property information of the object 100 may be displayed as shown in FIG. 12(b). When the device 200 is located within a predetermined distance from the object 100, the device 200 may receive the property information of the object 100 from the object 100 and display the received property information. The property information of the object 100 may include a model name of the object 100, a serial number of the object 100, URL information necessary for receiving services related to the object 100, and identifiers of recommended applications related to the object 100.

Furthermore, in the initial screen image of the application as shown in FIG. 12(a), when a predetermined icon included in the region 22 for displaying context information is selected, context information acquired by the device 200 may be displayed as shown in FIG. 12(c). The device 200 may display context information related to the intention information included in the region 24 for displaying intention information described below. The device 200 may display information related to a current location of the device 200, current time, job of a user, and family/acquaintances of the user.

Figure 13:
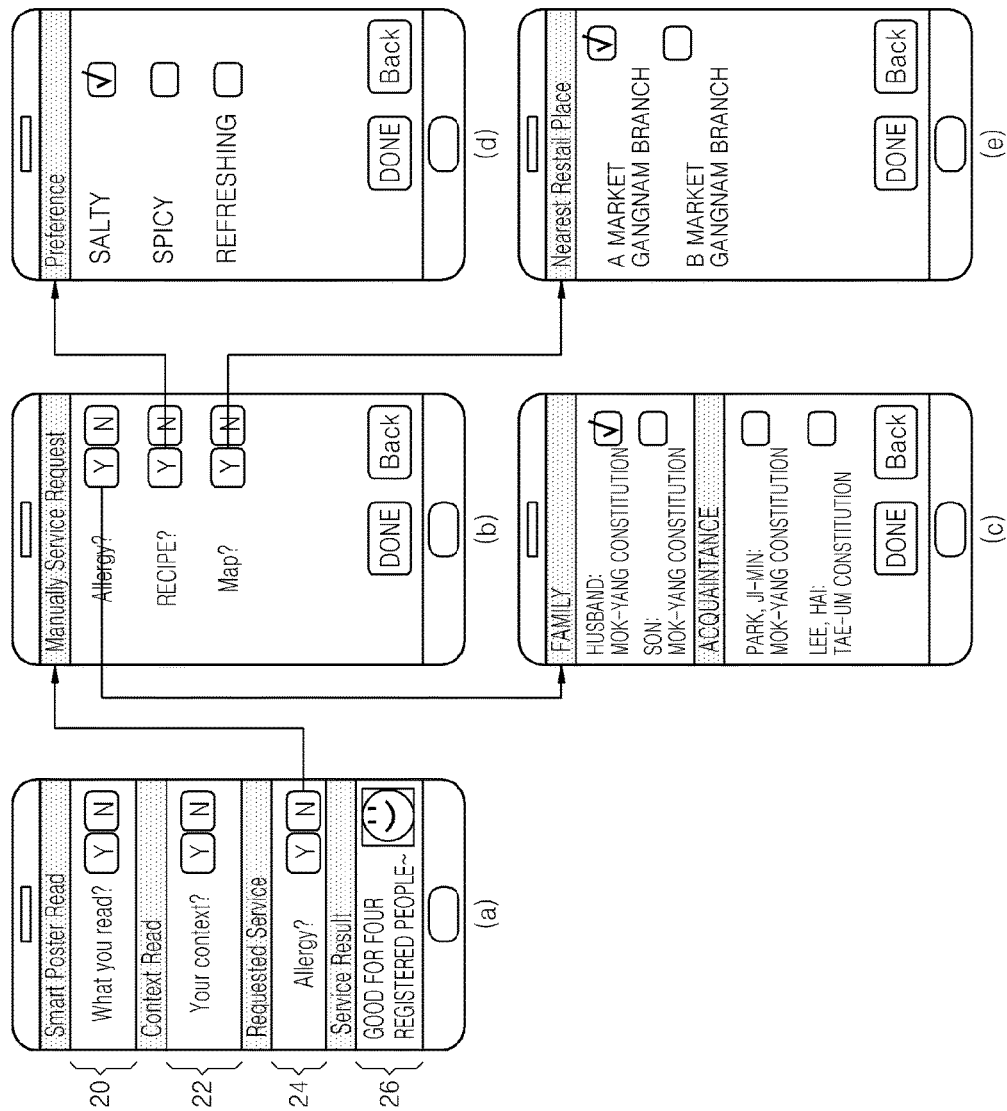
FIG. 13 is a diagram showing an example in which intention information related to a user is displayed and context information related to the determined intention information is displayed, according to an exemplary embodiment.

FIG. 13 is a diagram showing an example in which intention information related to a user is displayed and context information related to the determined intention information is displayed, according to an exemplary embodiment.

In the initial screen image of the application as shown in FIG. 13(a), the region 24 for displaying intention information may include at least one from between a service corresponding to intention of a user and types of specific information to be provided by the service. For example, the region 24 for displaying intention information may include an allergy information providing service.

Furthermore, when a predetermined icon in the region 24 for displaying intention information is selected, a list of services related to the object 100 may be displayed as shown in FIG. 13(b), and the device 200 may select a predetermined service based on a user input.

Furthermore, when a predetermined icon in the list of services as shown in FIG. 13(b) is selected, screen images displaying context information related to the corresponding service may be displayed as shown in FIGS. 13(b) through 13(d).

For example, when an icon related to 'Allergy' is selected in the screen image of FIG. 13(b), a screen image for selecting family/acquaintances of a user as context information related to an allergy information providing service may be displayed as shown in FIG. 13(c). In this case, constitutions of family members or acquaintances of the user may be displayed.

Furthermore, when an icon related to 'Recipe' is selected in the screen image of FIG. 13(b), a screen image for selecting taste preferences of a user as context information related to recipe providing service may be displayed as shown in FIG. 13(d). In this case, the taste preferences of the user may include at least one from among salty taste, spicy taste, and refreshing taste.

Furthermore, when an icon related to 'Map' is selected in the screen image of FIG. 13(b), a screen image for selecting a destination as context information related to navigation service may be displayed as shown in FIG. 13(e). For example, a destination may be recommended based on a current location of the device 200 or the object 100, e.g., A market Gangnam branch, B market Gangnam branch, etc.

Figure 14:
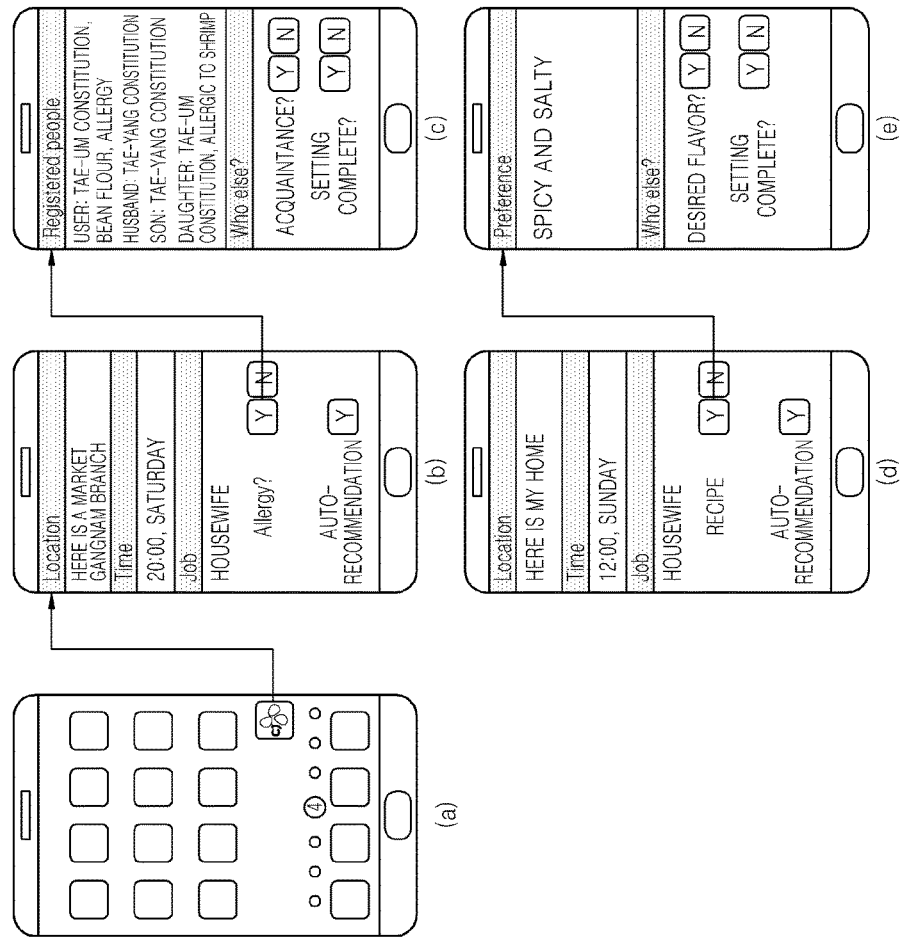
FIG. 14 is a diagram showing an example in which intention information related to a user is displayed and context information related to the determined intention information is displayed, according to another exemplary embodiment.

FIG. 14 is a diagram showing an example in which intention information related to a user is displayed and context information related to the determined intention information is displayed, according to another exemplary embodiment.

When a predetermined application is selected in the screen image as shown in FIG. 14(a), the device 200 may recommend context information and intention information based on at least one form between properties of the object 100 and the application as shown in FIG. 14(b). Referring to FIG. 14(b), the device 200 may display the current location of the device 200, current time, and job of a user as context information and may recommend an allergy information providing service as a type of service included in intention information.

If a user selects an icon related to 'Allergy' displayed on a screen image as shown in FIG. 14(b), a target of an allergy information providing service may be recommended on a screen image displayed on the device 200 as shown in FIG.

14(c). For example, the target of the allergy information providing service may include family members or acquaintances of the user.

Furthermore, when a predetermined application is selected in a screen image as shown in FIG. 14(a), the device 200 may recommend context information and intention information based on at least one from between properties of the object 100 and the application as shown in FIG. 14(b). Referring to FIG. 14(d), the device 200 may display the current location of the device 200, current time, and job of a user as context information and may recommend a recipe providing service as a type of service included in intention information.

If a user selects an icon related to 'Recipe' displayed on a screen image as shown in FIG. 14(d), types of specific information to be provided by the recipe providing service may be recommended on a screen image displayed on the device 200 as shown in FIG. 14(e). For example, the specific information to be provided by the recipe providing service may include a recipe having a spicy taste.

Figure 15:
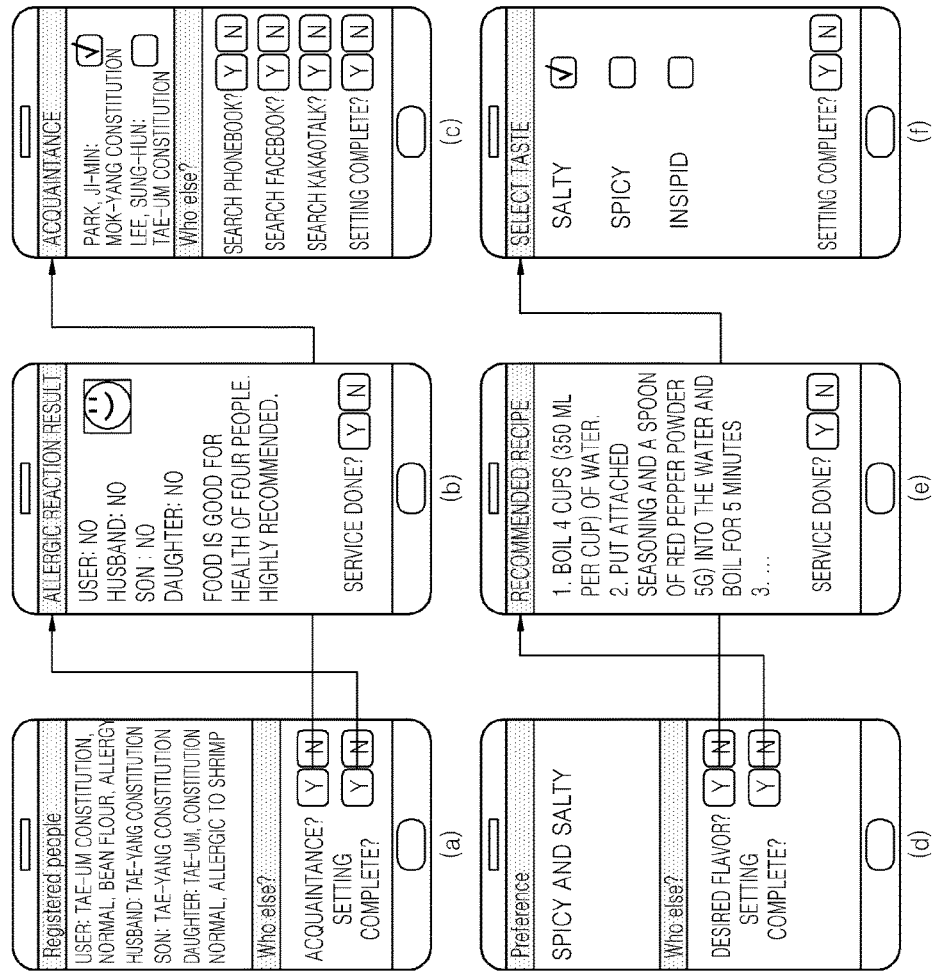
FIG. 15 is a diagram showing an example in which the device receives a service and changes intention information.

FIG. 15 is a diagram showing an example in which the device 200 receives a service and changes intention information.

When an icon for completing setup is selected in a screen image as shown in FIG. 15(a), a target for an allergy information providing service may be determined. Furthermore, as shown in FIG. 15(b), allergy information related to the determined target may be displayed in a screen image. Furthermore, when an icon for changing a target of the allergy information providing service is selected in the screen image as shown in FIG. 15(a), a screen image for changing the target of the allergy information providing service may be displayed as shown in FIG. 15(c). Referring to FIG. 15(c), the device 200 may select a predetermined target from a list of targets for the allergy information providing service or may search for a target via a SNS service.

Furthermore, when an icon for completing setup is selected in a screen image as shown in FIG. 15(d), a recipe for cooking a food having a spicy taste may be displayed in a screen image as shown in FIG. 15(e). Furthermore, when an icon for changing specific information to be provided by the recipe providing service is selected in a screen image as shown in FIG. 15(d), a screen image for selecting the taste of food may be displayed as shown in FIG. 15(f). Referring to FIG. 15(f), the device 200 may select a predetermined taste from a list of tastes.

Figure 16:
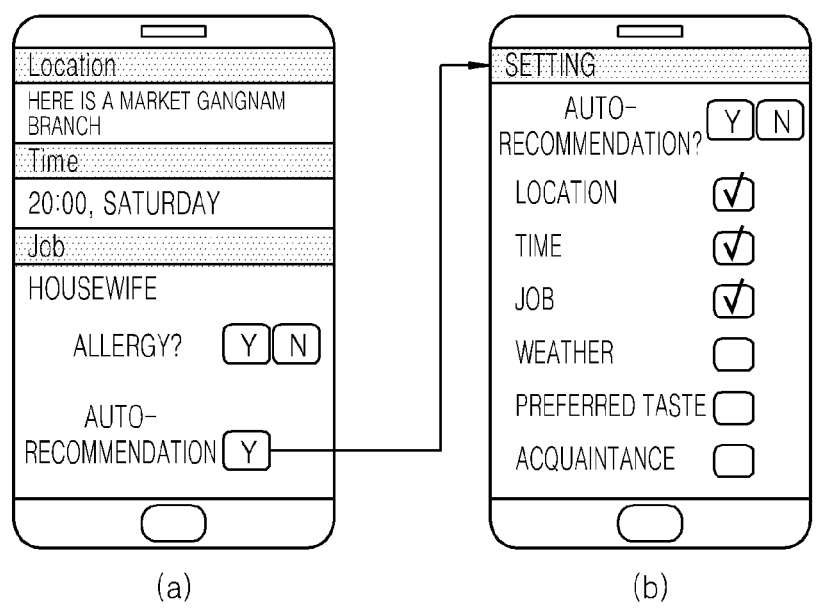
FIG. 16 is a diagram showing an example in which the device sets up context information used for providing a service based on a user input, according to an exemplary embodiment.

FIG. 16 is a diagram showing an example in which the device 200 sets up context information used for providing a service based on a user input, according to an exemplary embodiment.

In a screen image as shown in FIG. 16(a), the current location of the device 200, current time, and job of a user may be recommended as context information used for an allergy information providing service. Furthermore, when an icon for changing a list of recommendations is selected in the screen image as shown in FIG. 16(a), a list for selecting context information to be recommended may be displayed in a screen image as shown in FIG. 16(b).

Figure 17:
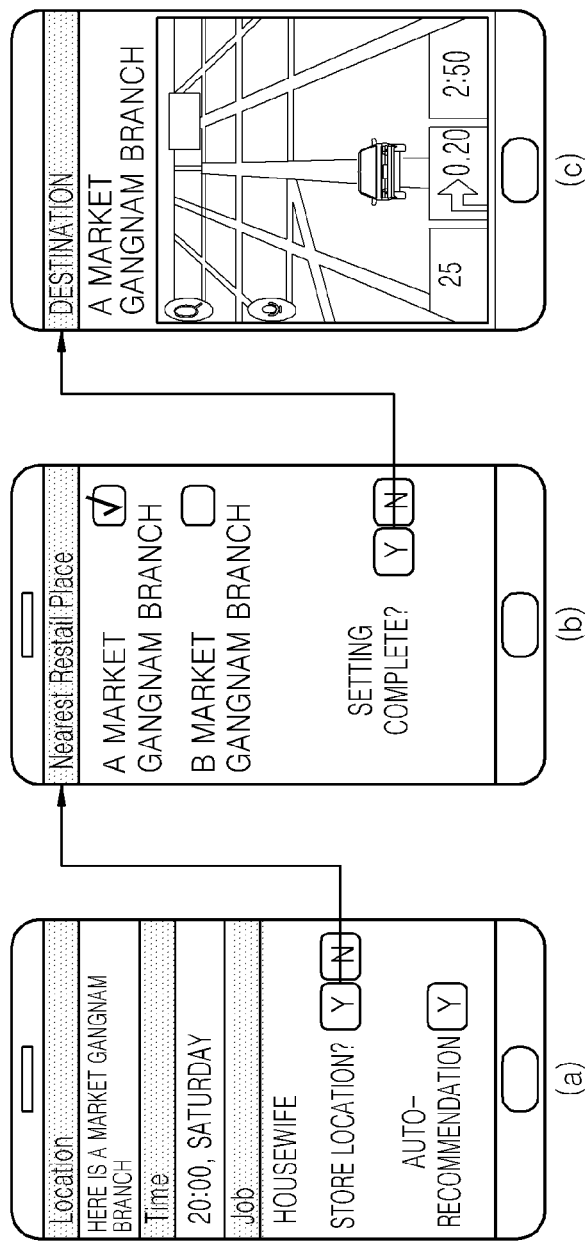
FIG. 17 is a diagram showing an example of providing a navigation service according to an exemplary embodiment.

FIG. 17 is a diagram showing an example of providing a navigation service according to an exemplary embodiment.

When the device 200 is located within a predetermined distance from the object 100, the device 200 may receive property information of the object 100 from the object 100 and acquire context information and intention information. For example, if the object 100 is an advertisement poster related to a 'soup,' when the device 200 approaches to the object 100, intention information and context information generated by the device 200 may be displayed in a screen image on the device 200 as shown in FIG. 17(a). For example, store location?' may indicate that a type of service included in the intention information corresponds to a navigation service. Furthermore, the current location of the device 200, current time, and job of a user, which are context information related to a navigation service, may be displayed.

Furthermore, when a user selects a predetermined icon, a list of recommended destinations may be displayed as shown in FIG. 17(b), and the user may select a predetermined destination.

Next, the device 200 may provide the property information of the object 100, the generated intention information, and context information related to the intention information to the server 300 and may receive navigation service from the server 300 as shown in FIG. 17(c).

Figure 18:
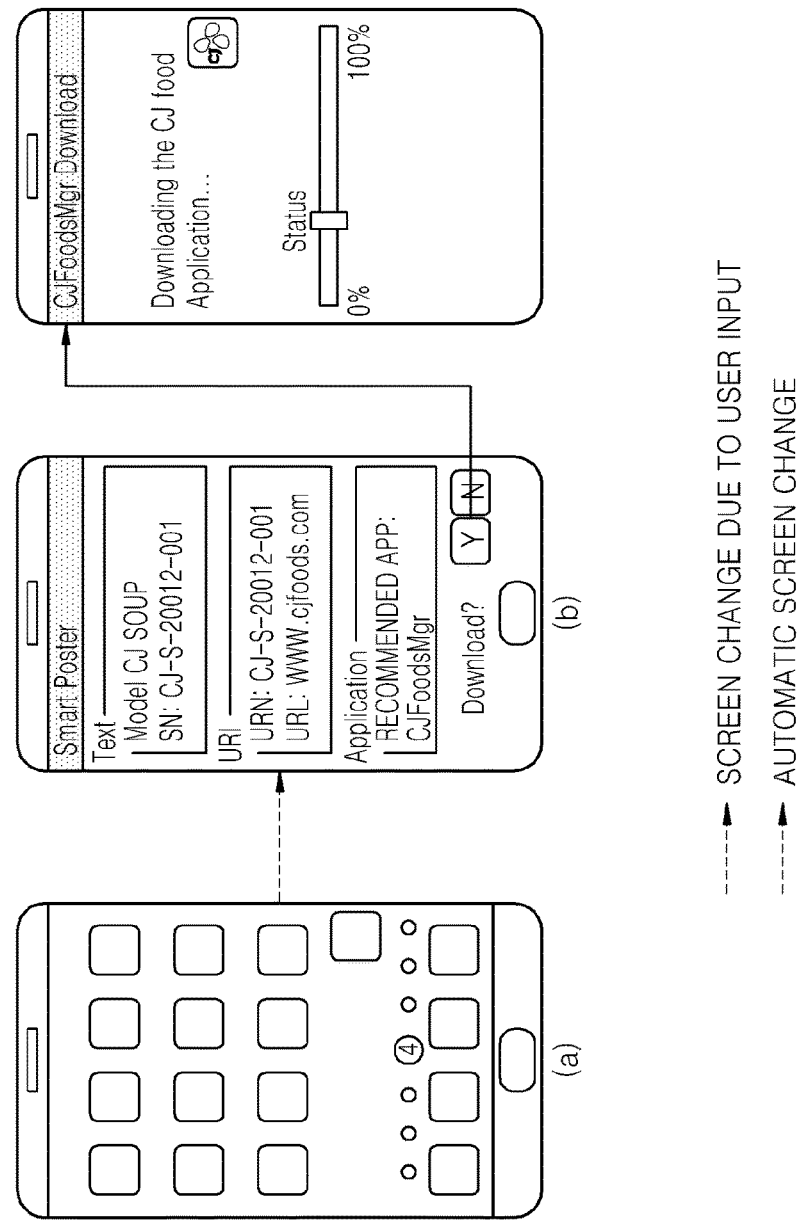
FIG. 18 is a diagram showing an example in which the device downloads an application based on application information included in the property information of the object.

FIG. 18 is a diagram showing an example in which the device 200 according to an exemplary embodiment downloads an application based on application information included in the property information of the object 100.

Referring to FIG. 18, when a predetermined icon is selected in a screen image on the device 200 as shown in FIG. 18(a), an initial screen image of an application for receiving services related to an object may be displayed as shown in FIG. 18(b). Furthermore, a list of recommended applications may be displayed in the initial screen image of the application, and a user may select an icon to download a corresponding application. Next, as shown in FIG. 18(c), the device 200 may download the selected application.

Figure 19:
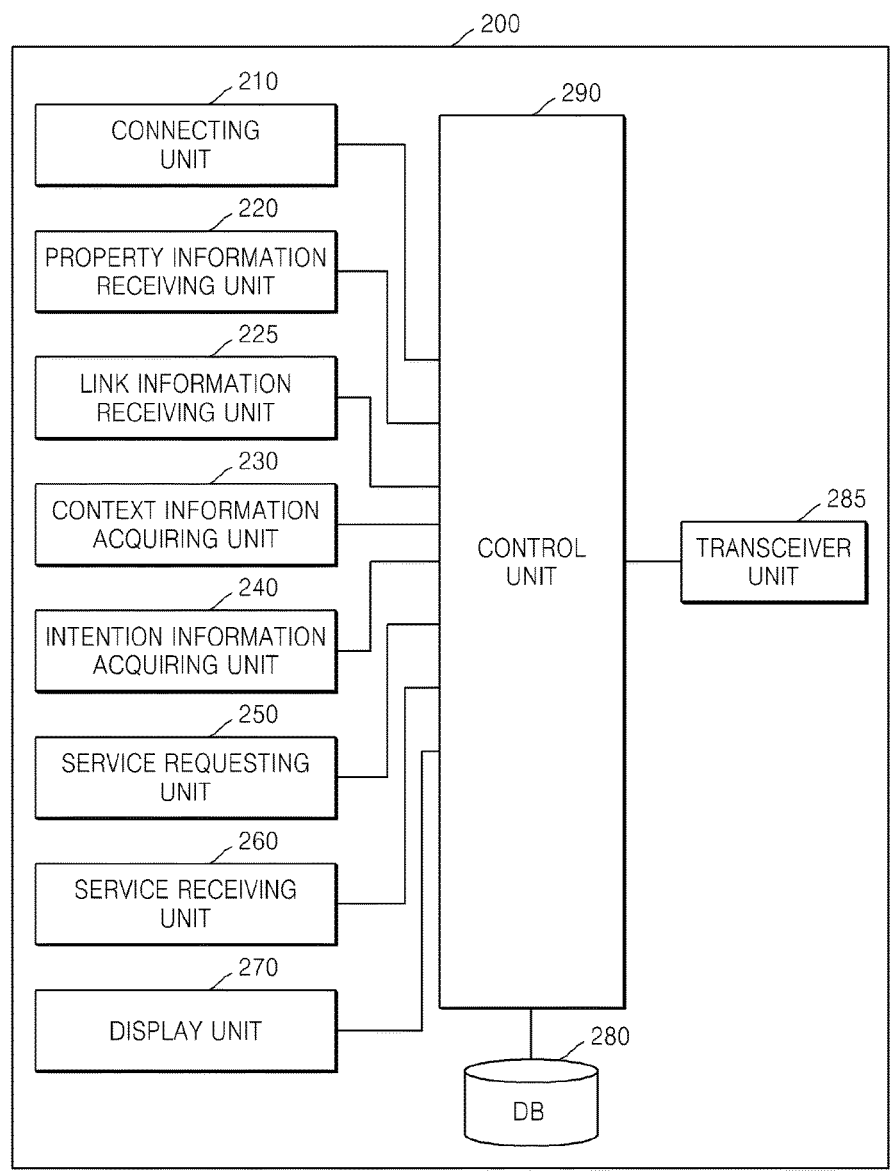
FIG. 19 is a block diagram of the device according to an exemplary embodiment.

FIG. 19 is a block diagram of the device 200 according to an exemplary embodiment.

As shown in FIG. 19, the device 200 according to an exemplary embodiment includes a connecting unit 210, a property information receiving unit 220, a link information receiving unit 225, a context information acquiring unit 230, an intention information acquiring unit 240, a service requesting unit 250, a service receiving unit 260, a display unit 270, a DB 280, a transceiver 285, and a control unit 290.

The connecting unit 210 connects the device 200 and the object 100 to each other via a communication network. When the device 200 approaches to the object 100, the connecting unit 210 may connect the device 200 to the object 100 via a close-distance communication network.

The property information receiving unit 220 receives the property information of the object 100 from the object 100. The property information of the object 100 is information related to properties of the object 100 and may include information regarding at least one from among an identifier of the object 100, a type of the object 100, applications related to the object 100, and services related to the object 100.

The link information receiving unit 225 receives link information from the object 100. The link information may include a link address of the server 300 which provides services related to the object 100.

The context information acquiring unit 230 acquires context information. The context information acquiring unit 230 may acquire context information based on intention information described below. For example, if the type of service included in the intention information is 'recipe providing service' and the type of specific information to be provided by the corresponding service is a 'recipe using an oven,' the context information acquiring unit 230 may acquire information regarding preferred tastes of a user as context information.

Although it is described above that context information is acquired based on intention information, the context information acquisition is not limited thereto. The context information acquiring unit 230 may acquire context information related to the device 200 and context information related to a user in advance and may extract context information related to intention information from the pre-acquired context information. In this case, the pre-acquired context information may be used by the intention information acquiring unit 240 to generate intention information.

Furthermore, the context information acquiring unit 230 may acquire context information based on an application that is either being executed or is executed by the device 200. For example, if an application that is being executed by the device 200 is an application for receiving recipes, context information related to recipes may be acquired.

In this case, an application for receiving services may be executed based on application information included in the property information of the object 100. If an application for receiving services is not installed on the device 200, the device 200 may download a predetermined application and install the downloaded application. Furthermore, if an application for receiving services is installed on the device 200, the device 200 may execute the installed application. Although it is described above that an application is executed after the device 200 approaches the object 100 and receives property information of the object 100, the exemplary embodiment is not limited thereto. An application for receiving services may be executed by the device 200 in advance, and the device 200 may approach the object 100 and receive property information of the object 100 from the object 100 while the application is being executed.

The intention information acquiring unit 240 generates intention information based on properties of the object 100. The intention information is information related to services a user wants to receive and may include information regarding types of services and types of specific information to be provided by the services.

The intention information acquiring unit 240 may determine types of services based on properties of the object 100 and may determine types of specific information to be provided by the determined services. For example, if the object 100 is an advertisement poster related to 'soup,' the intention information acquiring unit 240 may select one from among an allergic reaction checking service, a recipe providing service, and a navigation service.

If the intention information acquiring unit 240 selects the recipe providing service, the intention information acquiring unit 240 may determine specific information to be provided by the recipe providing service. For example, the specific information to be provided by the recipe providing service may include a recipe using an oven, a recipe using a microwave, and a recipe using a gas stove, and the device 200 may select the recipe using a microwave.

Types of services and types of specific information to be provided by services may be determined based on properties of the object 100 and user inputs. However, the services and information are not limited thereto, and types of services and types of specific information to be provided by services may be determined based on context information as described below. Furthermore, the intention information acquiring unit 240 may determine only types of services and may not determine specific information to be provided by services.

Furthermore, the intention information acquiring unit 240 may determine types of services based on the current location of the device 200 and applications being executed and may determine types of specific information to be provided by the determined services.

The intention information acquiring unit 240 may also receive intention information generated by the object 100 from the object 100. In this case, information necessary for generating the intention information may be provided to the object 100 by the device 200 in advance.

The service requesting unit 250 requests the server 300 for a predetermined service. The service requesting unit 250 may provide property information of the object 100 and intention information and context information acquired by the device 200 to the server 300. The service requesting unit 250 may receive a request for acquired context information from the object 100 and may provide the context information to the object 100 in response. For example, the service requesting unit 250 may provide information indicating that the object 100 is a smart poster related to 'soup,' a 'recipe providing service' and a 'recipe using an oven' are necessary, and a user prefers spicy taste to the server 300.

Furthermore, the service requesting unit 250 may request the object 100 to provide services.

The service receiving unit 260 receives a service from the server 300. For example, the service receiving unit 260 may receive information regarding a recipe for using an 'oven' to cook a 'soup' having a 'spicy taste' from the server 300.

Furthermore, the service receiving unit 260 may receive a service from the object 100. Furthermore, the service receiving unit 260 may receive a service provided by the server 300 via the object 100.

The display unit 270 displays various information related to operations of the device 200 in a screen image. The display unit 270 may display a user interface for requesting and receiving a service and specific information provided by the service.

The DB 280 stores various information necessary for the device 200 to acquire intention information and context information and to receive a service from the server 300.

The transceiver unit 285 transmits and receives various information from and to the server 300 and the object 100. The various information may be information necessary for the device 200 to acquire intention information and context information and to receive a services from the server 300.

The control unit 290 controls the overall operations of the device 200 and controls the connecting unit 210, the property information receiving unit 220, the link information receiving unit 225, the context information acquiring unit 230, the intention information acquiring unit 240, the service requesting unit 250, the service receiving unit 260, the display unit 270, the DB 280, and the transceiver unit 285 for the device 200 to receive various information necessary for acquiring intention information and context information and receiving a service from the server 300.

All or some of the connecting unit 210, the property information receiving unit 220, the link information receiving unit 225, the context information acquiring unit 230, the intention information acquiring unit 240, the service requesting unit 250, the service receiving unit 260, and the display unit 270 may be operated by software modules. However, the units of the device 200 are not limited thereto. Furthermore, the connecting unit 210, the property information receiving unit 220, the link information receiving unit 225, the context information acquiring unit 230, the intention information acquiring unit 240, the service requesting unit 250, the service receiving unit 260, and the display unit 270 may be operated by hardware modules.

Furthermore, the connecting unit 210, the property information receiving unit 220, the link information receiving unit 225, the context information acquiring unit 230, the intention information acquiring unit 240, the service requesting unit 250, the service receiving unit 260, and the display unit 270 may be included in the control unit 290, and the connecting unit 210, the property information receiving unit 220, the link information receiving unit 225, the context information acquiring unit 230, the intention information acquiring unit 240, the service requesting unit 250, the service receiving unit 260, the display unit 270, and the control unit 290 may be operated by a single processor. However, the device 200 is not limited thereto.

Figure 20:
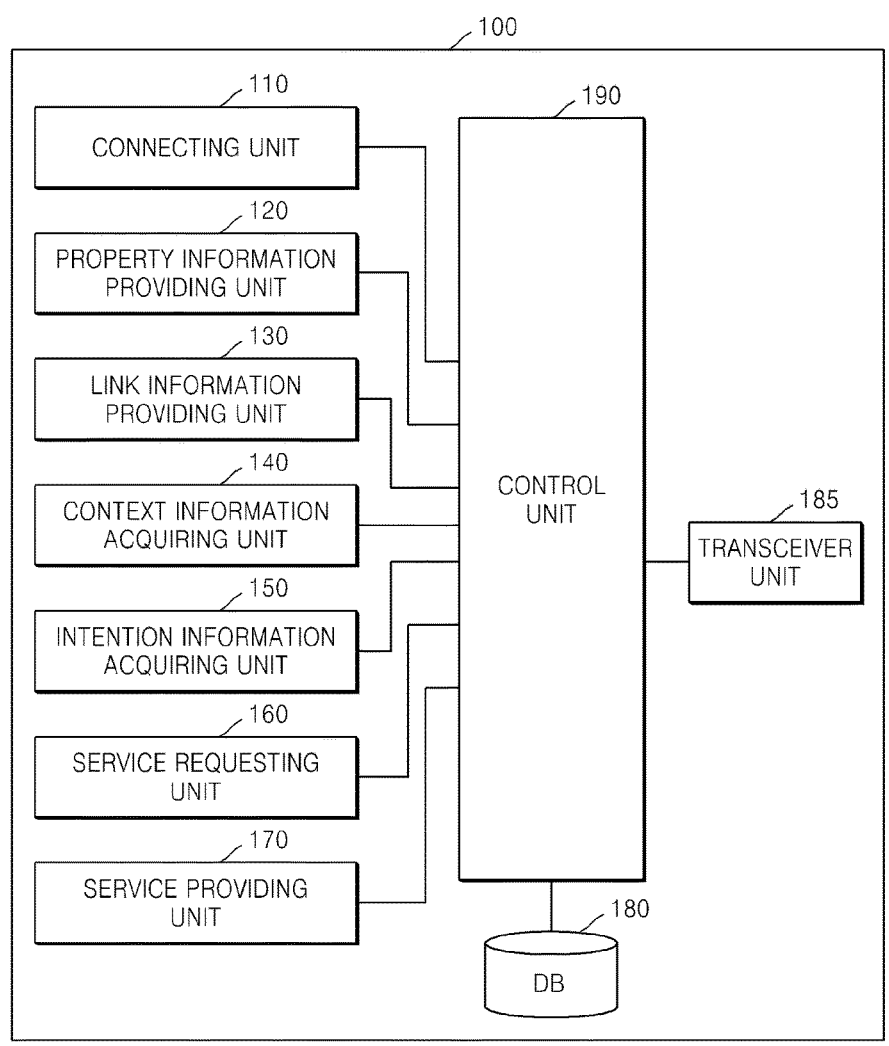
FIG. 20 is a block diagram of the object according to an exemplary embodiment.

FIG. 20 is a block diagram of the object 100 according to an exemplary embodiment.

As shown in FIG. 20, the object 100 according to an exemplary embodiment includes a connecting unit 110, a property information providing unit 120, a link information providing unit 130, a context information acquiring unit 140, an intention information acquiring unit 150, a service requesting unit 160, a service providing unit 170, a DB 180, a transceiver unit 185, and a control unit 190.

The connecting unit 110 connects the device 200 and the object 100 to each other via a communication network. When the device 200 approaches to the object 100, the connecting unit 110 may connect the device 200 to the object 100 via a close-distance communication network.

The property information providing unit 120 receives the property information of the object 100 from the object 100, and the link information providing unit 130 provides link information to the device 200.

The context information acquiring unit 140 acquires context information acquired by the device 200 from the device 200. Furthermore, the context information acquiring unit 140 may extract context information related to intention information from the intention information as described below The intention information acquiring unit 150 acquires intention information. The intention information acquiring unit 150 may determine types of services based on properties of the object 100 and may determine types of specific information to be provided by the services. Furthermore, the intention information acquiring unit 150 may acquire intention information based on context information. The intention information acquiring unit 150 may also acquire intention information based on a user input. In this case, the intention information acquiring unit 150 may acquire intention information based on at least one of user input signals provided by the device 200 and user input signals via an input unit of the object 100. The intention information acquiring unit 150 may determine types of services based on the properties of the object 100 and the current location of the device 200 and determine types of specific information to be provided by the determined services.

The service requesting unit 160 may request the server 300 to provide a predetermined service to the device 200. The service requesting unit 160 may provide property information, intention information, and context information to the server 300. For example, the service requesting unit 160 may provide information indicating that the object 100 is a smart poster related to 'soup', a 'recipe providing service' and a 'recipe using an oven' are necessary, and a user prefers spicy taste to the server 300.

Furthermore, the service requesting unit 160 may provide information necessary to request services to the device 200. In this case, the device 200 may request the server 300 to provide services.

The service providing unit 170 provides services to the device 200. If specific information in relation to services are stored in the object 100, the service providing unit 170 may provide predetermined services to the device 200.

Furthermore, the service providing unit 170 may receive services provided by the server 300 and provide the received services to the device 200.

The DB 180 stores various information necessary for the object 100 to acquire intention information and context information and to request or provide services.

The transceiver unit 185 transmits and receive various information necessary for the object 100 to acquire intention information and context information, request services from the server 300, or provide services to the device 200.

The control unit 190 controls the overall operations of the object 100 and controls the connecting unit 110, the property information providing unit 120, the link information providing unit 130, the context information acquiring unit 140, the intention information acquiring unit 150, the service requesting unit 160, the service receiving unit 170, the DB 180, and the transceiver unit 185 for the object 100 to receive various information necessary for acquiring intention information and context information and requesting or providing a service.

The connecting unit 110, the property information providing unit 120, the link information providing unit 130, the context information acquiring unit 140, the intention information acquiring unit 150, the service requesting unit 160, and the service providing unit 170 may be operated by software modules. However, the object 100 is not limited thereto. Furthermore, the connecting unit 110, the property information providing unit 120, the link information providing unit 130, the context information acquiring unit 140, the intention information acquiring unit 150, the service requesting unit 160, and the service providing unit 170 may be operated by hardware modules.

Furthermore, the connecting unit 110, the property information providing unit 120, the link information providing unit 130, the context information acquiring unit 140, the intention information acquiring unit 150, the service requesting unit 160, the service providing unit 170 may be included in the control unit 190. The connecting unit 110, the property information providing unit 120, the link information providing unit 130, the context information acquiring unit 140, the intention information acquiring unit 150, the service requesting unit 160, the service providing unit 170, and the control unit 190 may be operated by a single processor. However, the object 100 is not limited thereto.

Figure 21:
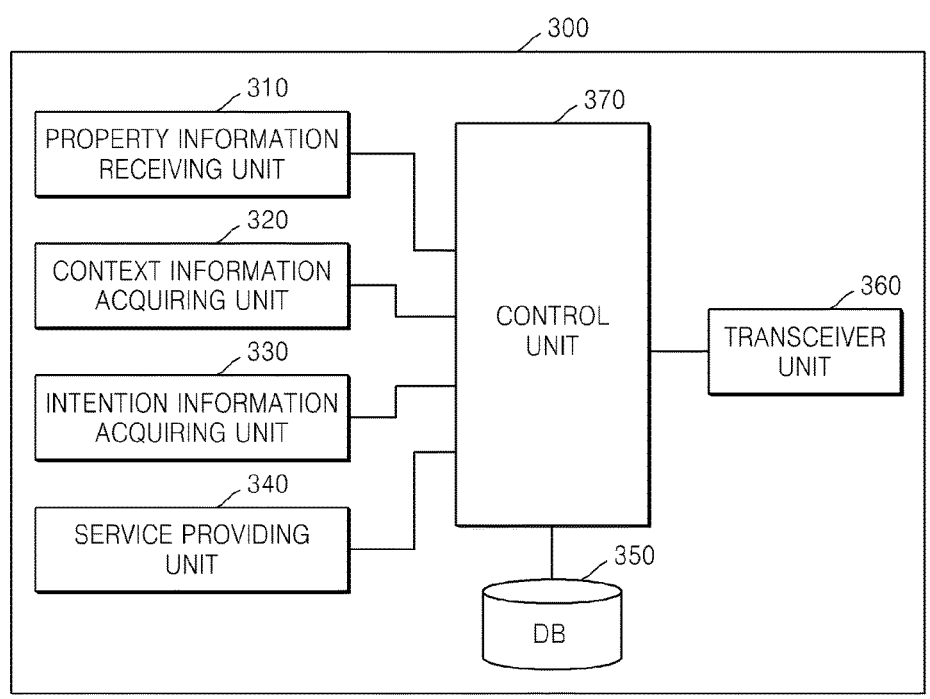
FIG. 21 is a block diagram of the server according to an exemplary embodiment.

FIG. 21 is a block diagram of the server 300 according to an exemplary embodiment.

As shown in FIG. 21, the server 300 according to an exemplary embodiment includes a property information receiving unit 310, a context information acquiring unit 320, an intention information acquiring unit 330, a service providing unit 340, a DB 350, a transceiver unit 360, and a control unit 370.

The property information receiving unit 310 receives the property information of the object 100 from the device 200. However, the property information reception is not limited thereto. If the object 100 generates intention information, the property information receiving unit 310 may receive context property information from the object 100.

The context information acquiring unit 140 receives context information from the device 200. However, the context information reception is not limited thereto. If the object 100 generates intention information, the context information acquiring unit 320 may receive context information from the object 100.

Furthermore, if the server 300 generates intention information, the server 300 may extract context information related to the intention information from context information received from the device 200.

The intention information acquiring unit 330 acquires intention information. The intention information acquiring unit 330 may determine types of services based on properties of the object 100 and may determine types of specific information to be provided by the services. Furthermore, the intention information acquiring unit 330 may acquire intention information based on context information. The intention information acquiring unit 330 may also acquire intention information based on a user input. In this case, the intention information acquiring unit 330 may acquire intention information based on at least one from between user input signals provided by the device 200 and user input signals via an input unit of the object 100.

Furthermore, the intention information acquiring unit 330 may determine types of services based on the properties of the object 100 and current location of the device 200 and determine types of specific information to be provided by the determined services.

The service providing unit 340 provides services to the device 200. The service providing unit 340 may provide services to the device 200 in response to a service providing request from the device 200 or the object 100.

Furthermore, the service providing unit 340 may provide services to the device 200 via the object 100.

The DB 350 stores various information necessary for the server 300 to provide services to the device 200.

The transceiver unit 360 transmits and receives various information necessary for the server 300 to provide services to the device 200.

The control unit 370 controls the overall operations of the server 300 and controls the property information receiving unit 310, the context information acquiring unit 320, the intention information acquiring unit 330, the service providing unit 340, the DB 350, and the transceiver unit 360 for the server 300 to provide services to the device 200.

The property information receiving unit 310, the context information acquiring unit 320, the intention information acquiring unit 330, and the service providing unit 340 may be operated by software modules. However, the server 300 is not limited thereto. Furthermore, the property information receiving unit 310, the context information acquiring unit 320, the intention information acquiring unit 330, and the service providing unit 340 may be operated by hardware modules.

Furthermore, the property information receiving unit 310, the context information acquiring unit 320, the intention information acquiring unit 330, and the service providing unit 340 may be included in the control unit 370, and the property information receiving unit 310, the context information acquiring unit 320, the intention information acquiring unit 330, the service providing unit 340, and the control unit 370 may be operated by a single processor. However, the server 300 is not limited thereto.

The methods and functions of the exemplary embodiments may be implemented in the form of a recording medium that includes computer executable instructions, such as program modules, being executed by a computer. Computer-readable media can be any available media that can be accessed by the computer and includes both volatile and nonvolatile media, removable and non-removable media. In addition, the computer-readable media may include computer storage media and communication media. Computer storage media includes both the volatile and non-volatile, removable and non-removable media implemented as any method or technology for storage of information such as computer readable instructions, data structures, program modules, or other data. The medium of communication is typically computer-readable instructions, and other data in a modulated data signal such as data structures, program modules, or carrier, or other transport mechanism and includes any information delivery media.

While the exemplary embodiments have been particularly shown and described, it will be understood by those skilled in the art that various changes in form and details may be made therein without departing from the spirit and scope of the invention as defined by the appended claims. The preferred embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A method by which a device receives a service associated with an object, the method comprising:
   forming a communication network including the device and the object, when the device is located within a near field communication range from the object;
   receiving property information of the object from the object connected to the device via the communication network;
   determining types of services based on the received property information and a current location of the device;
   transmitting the determined types of services to the object;
   sending a request directly from the object to a server for an available service based on the types of services and the property information of the object; and
   receiving the available service requested by the object from the server.

2. The method of claim 1, wherein the determining comprises determining types of specific information to be provided by the available service based on the received property information and the current location of the device; and
   wherein the sending comprises sending a request from the object to the server for the available service based on the types of the specific information.

3. The method of claim 2, further comprising acquiring context information related to the types of the available service and the types of the specific information,
   wherein the sending the request from the object to the server for the available service based on the types of the available service and the types of the specific information comprises providing the acquired context information to the object.

4. The method of claim 3, wherein the receiving comprises receiving the service based on the types of the available service, the types of the specific information, and the context information.

5. The method of claim 3, wherein the acquiring comprises acquiring context information related to an application being executed by the device.

6. The method of claim 3, wherein the context information comprises information related to at least one of a date, a time, the current location of the device, a gender of a user, an age of the user, and an execution history of an application that is executed by the device in relation to the available service.

7. The method of claim 3, wherein the acquired context information is provided to the server via the object.

8. The method of claim 3, wherein sending the request comprises requesting the server for the available service based on time, a user profile of the user, and a user history of services used by the user.

9. The method of claim 1, wherein the property information of the object comprises information related to services associated with the object and at least one of an identifier of the object and information related to applications related to the services.

10. The method of claim 1, wherein the receiving comprises receiving the property information via a close-distance communication network.

11. The method of claim 1, wherein the property information is property information related to an object selected based on a user input via the device.

12. The method of claim 1, wherein the property information is provided by the object to the device based on a user input for selecting from a predetermined list displayed on a screen of the object.

13. The method of claim 1, wherein the receiving comprises receiving specific information to be provided by a type of service selected based on the received property information and the current location of the device from the server.

14. The method of claim 1, wherein the sending the request comprises requesting the available service from the server via the object,
the receiving comprises receiving from the server specific information to be provided by a type of service selected based on the received property information of the object and the current location of the device, and
the specific information to be provided by the type of service selected based on the received property information and the current location of the device is determined by the object.

15. A method by which a device receives a service associated with an object, the method comprising:
forming a communication network including the device and the object, when the device is located within a near field communication range from the object;
determining an application executed by the device and receiving property information of the object from the object connected to the device via the communication network;
sending a request directly from the object to a server to provide an available service based on types of services provided by the application and a current location of the device; and
receiving the available service requested by the object, from the server.

16. The method of claim 15, wherein the sending a request of the available service comprises:
determining types of the available service and types of specific information to be provided by the available service based on the received property information and the current location of the device; and
requesting the server for the available service based on the types of the available service and the types of the specific information.

17. The method of claim 16, further comprising acquiring context information related to the types of the available service and the types of the specific information, wherein the sending a request to the server for the available service based on the types of the available service and the types of the specific information comprises providing the acquired context information to the server.

18. The method of claim 17, wherein the receiving comprises receiving the service based on the types of the available service, the types of the specific information, and the context information.

19. The method of claim 17, wherein the context information comprises information related to at least one of a date, a time, the current location of the device, a gender of a user, an age of the user, and an execution history of an application that is executed by the device in relation to the available service.

20. The method of claim 17, wherein the acquired context information is provided to the server via the object.

21. The method of claim 3, wherein the sending a request comprises requesting the server for the available service based on time, a user profile of the user, and a user history of services used by the user.

22. A method by which an object provides a service associated with the object to a device, the method comprising:
forming a communication network including the device and the object, when the device is located within a near field communication range from the object;
transmitting property information of the object to the device connected to the object via the communication network;
receiving types of services which are determined by the device based on the property information and a current location of the device; and
sending a request, by the object, directly to a server for an available service based on the types of services and the property information of the object,
wherein the available service requested by the object is transmitted from the server to the device.

23. An object which provides a service related to the object, the object comprising:
a control unit configured to:
form a communication network including a device and the object, when the device is located within a near field communication range from the object,
transmit property information of the object to the device connected to the object via the communication network,
receive types of services which are determined by the device based on the property information and a current location of the device; and
send a request, by the object, directly to a server for an available service based on the types of services and the property information of the object,
wherein the available service requested by the object is transmitted from the server to the device.

24. A non-transitory computer readable recording medium having recorded thereon a computer executable program for implementing the method of claim 1.

25. A non-transitory computer readable recording medium having recorded thereon a computer executable program for implementing the method of claim 15.

26. A non-transitory computer readable recording medium having recorded thereon a computer executable program for implementing the method of claim 22.

* * * * *